United States Patent
Kim et al.

(10) Patent No.: US 12,029,924 B2
(45) Date of Patent: Jul. 9, 2024

(54) METHOD FOR INCREASING VIABILITY OF CELL BY IRRADIATING CELL WITH ULTRASONIC WAVES AND ULTRASONIC IRRADIATION APPARATUS USING SAME

(71) Applicant: BIOINFRA LIFE SCIENCE INC., Seoul (KR)

(72) Inventors: Chul Woo Kim, Seoul (KR); Dong Hee Park, Seoul (KR); Jong Ho Won, Seoul (KR); Hea Ry Oh, Seoul (KR)

(73) Assignee: BioInfra Life Science Inc., Seoul (KR)

( * ) Notice: Subject to any disclaimer, the term of this patent is extended or adjusted under 35 U.S.C. 154(b) by 489 days.

(21) Appl. No.: 17/290,490

(22) PCT Filed: Oct. 31, 2019

(86) PCT No.: PCT/KR2019/014611
§ 371 (c)(1),
(2) Date: Apr. 30, 2021

(87) PCT Pub. No.: WO2020/091464
PCT Pub. Date: May 7, 2020

(65) Prior Publication Data
US 2021/0379408 A1    Dec. 9, 2021

(30) Foreign Application Priority Data

Oct. 31, 2018 (KR) .................. 10-2018-0132627
Oct. 31, 2019 (KR) .................. 10-2019-0137552

(51) Int. Cl.
*A61N 7/00* (2006.01)

(52) U.S. Cl.
CPC ........ *A61N 7/00* (2013.01); *A61N 2007/0034* (2013.01); *A61N 2007/0073* (2013.01)

(58) Field of Classification Search
CPC .............................................. A61N 2007/0034
See application file for complete search history.

(56) References Cited

U.S. PATENT DOCUMENTS

2003/0229331 A1* 12/2003 Brisken ............. A61M 37/0092
                                                                    600/459
2011/0269693 A1* 11/2011 Luebcke .................. A61P 3/04
                                                                    601/2
2014/0257146 A1    9/2014 Kost et al.

FOREIGN PATENT DOCUMENTS

WO        9934858 A1    7/1999
WO    2017080891 A1    5/2017

OTHER PUBLICATIONS

Fan et al., 2014 "Characterization of the Dynamic Activities of a Population of Microbubbles Driven by Pulsed Ultrasound Exposure in Sonoporation," Ultrasound in Med & Biol 40(6):1260-72.
(Continued)

*Primary Examiner* — Jason M Ip
(74) *Attorney, Agent, or Firm* — Husch Blackwell LLP

(57) ABSTRACT

Disclosed are a method for increasing the viability of a cell by irradiating the cell with ultrasonic waves, and an ultrasound irradiation apparatus using same, wherein in a state where each of ultrasonic parameters is preconfigured in a predetermined range, the ultrasonic irradiation apparatus places an ultrasonic generation unit within a threshold range from the epidermis of an object to irradiate the epidermis of the object with ultrasonic waves, the ultrasonic parameters include at least a pressure of ultrasonic waves and a duty percentage of the ultrasonic waves, the pressure of the ultrasonic waves is 0.5 MPa to 1 MPa, and the duty percentage of the ultrasonic waves is 1% to 5%.

2 Claims, 33 Drawing Sheets

(56) References Cited

OTHER PUBLICATIONS

Sasaki and Takiguchi, 2018 "Low intensity pulsed ultrasound stimulates hair follicle cells in 3D culture," J Ther Ultrasound 6(Suppl 1):P21 (122 pages; see P21 on p. 68).
International Search Report from related International Application No. PCT/KR2019/014611, dated Feb. 13, 2020 (4 pages).
Written Opinion from related International Application No. PCT/KR2019/014611, dated Feb. 13, 2020 (4 pages).

* cited by examiner

PERIOD = 1/FREQUENCY
PERIOD = $T_{ON}$ + $T_{OFF}$
DUTY PERCENTAGE = $T_{ON}/(T_{ON}+T_{OFF})*100$

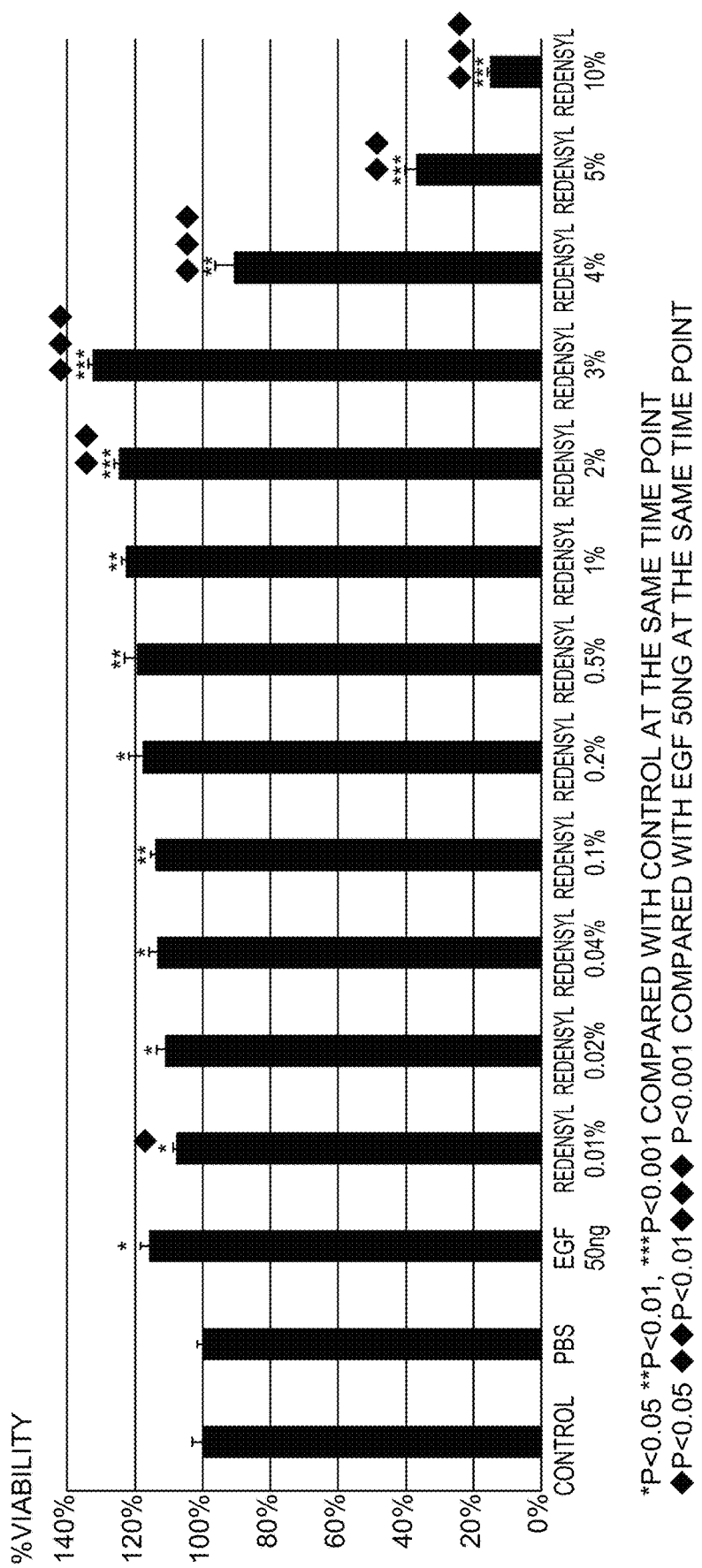

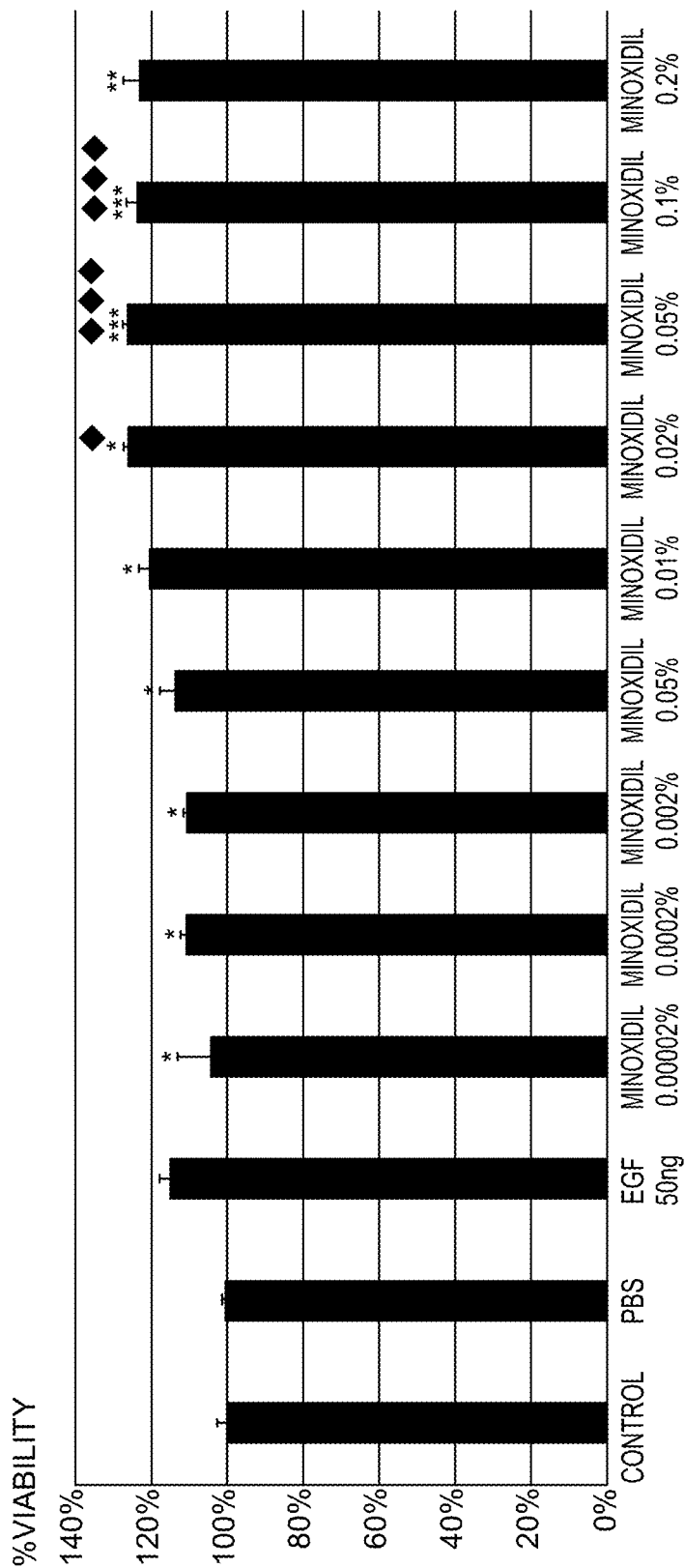

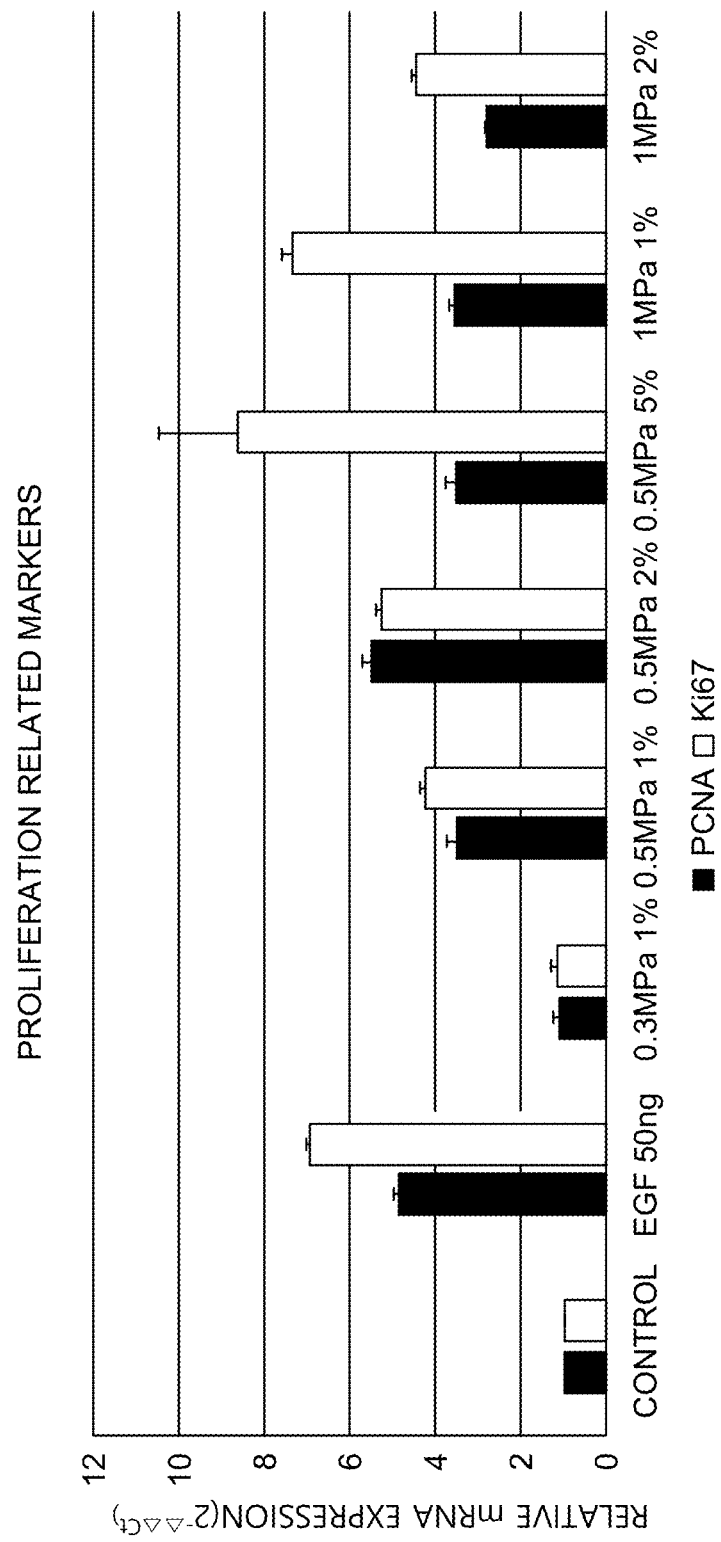

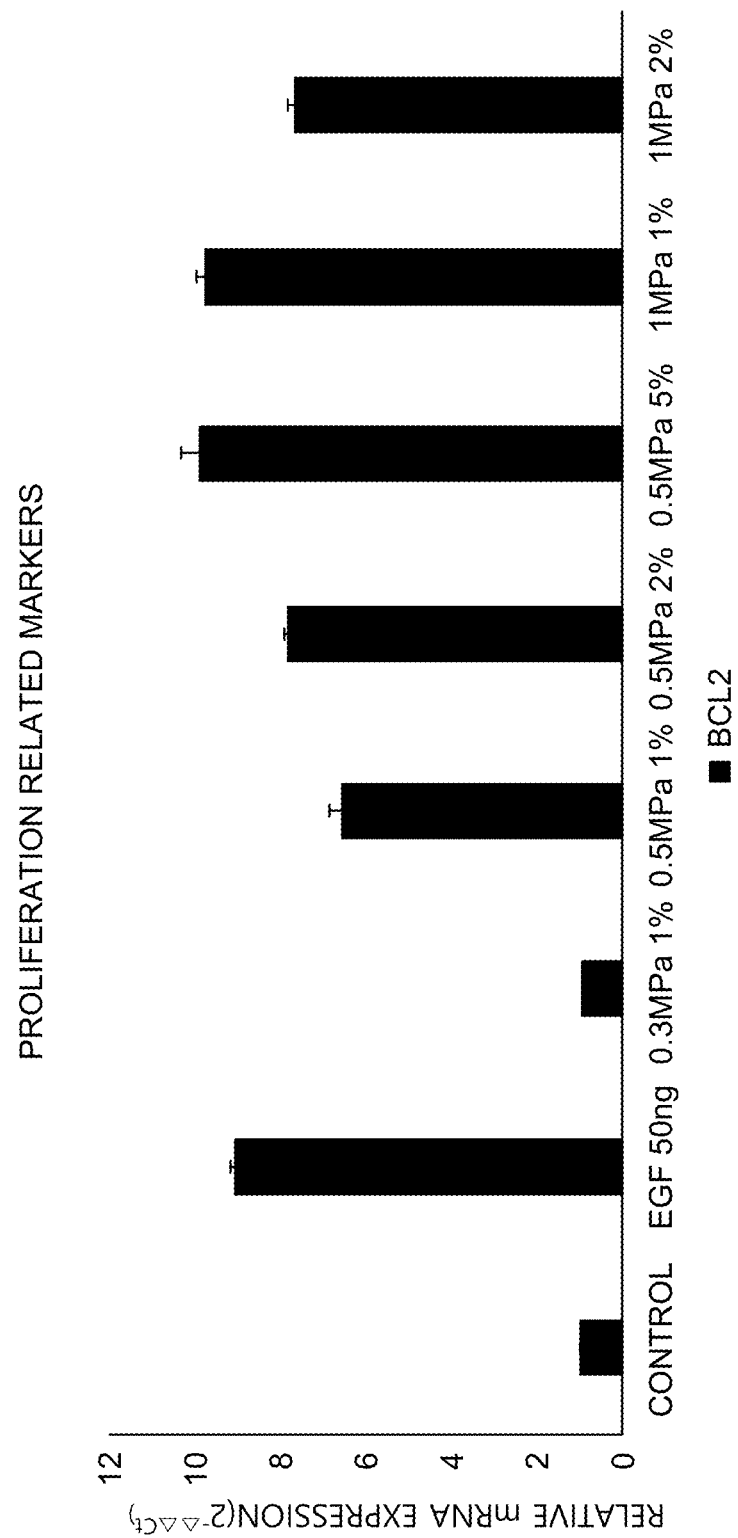

METHOD FOR INCREASING VIABILITY OF CELL BY IRRADIATING CELL WITH ULTRASONIC WAVES AND ULTRASONIC IRRADIATION APPARATUS USING SAME

1. FIELD OF THE DISCLOSURE

The present disclosure relates to a method for increasing a viability of cells by irradiating the cells with ultrasound and an ultrasound irradiating device using the same.

2. BACKGROUND OF THE DISCLOSURE

Minoxidil and Propecia are substances used as hair growth promoters. Minoxidil is a formulation applied to a scalp, and was developed by Pfizer as a treatment for hypertension due to its vasodilating effect, but is marketed as a hair loss treatment after a study on side effects of hair development on a forehead or a back of a hand. The mechanism by which minoxidil promotes hair growth is not fully understood, but it is theoretically known that minoxidil widens blood vessels in the scalp, opens potassium channels in cell membranes, and provides more oxygen and nutrients to follicles and thus inhibits hair loss, promotes hair growth, and thickens hair. But common side effects include redness, dry scalp, heart palpitations, tachycardia, and arrhythmia, etc.

Propecia sold by Merck is a brand name of finasteride which was originally developed to treat prostatic hyperplasia, but is used as the hair loss treatment because it promotes hair growth. 5α-reductase converts testosterone, i.e., male hormone, into dihydrotestosterone (DHT) which plays a major role in causing the hair loss. Finasteride reduces concentration of DHT that causes the hair loss by inhibiting the 5α-reductase enzyme. Typical side effects include decreased sexual functions, such as impotence, decreased libido, and a sexual arousal disorder, etc., and dizziness, a headache, a swelling, and a skin rash, etc. Men with infertility or low sperm count should pay attention to taking the drugs. In addition, there is a risk of birth defects, so women of childbearing age should not take or contact the drugs, and there are restrictions on prescription.

In addition, Avodart is a brand name of dutasteride family and, like finasteride, was developed as a treatment for the prostatic hyperplasia, but has been found to have an effect of preventing hair loss and is used as the hair loss treatment. In general, dutasteride is known to have a slightly stronger inhibitory effect against the hair loss than finasteride does. However, side effects such as the decreased libido, decreased kidney functions etc. are also known to be strong, so it is used less than finasteride, and has not been approved by the FDA as the hair loss treatment in the United States.

There are a number of raw materials included in functional cosmetics for preventing the hair loss, such as Redensyl, but those are peptides and growth factors, and most of them have high molecular weights (for example, 0.5 to 10 kDa). Therefore, when applied directly to a skin, the raw materials do not penetrate the skin well enough due to its low skin absorption rate.

Even if an existing drug delivery system (DDS) is used, only raw materials with low molecular weights (<500 Da) are partially absorbed due to the low skin absorption rate. Also, a deviation in the absorption rate is large depending on characteristics, such as hydrophilicity, hydrophobicity or poor solubility, etc., of the raw materials.

Iontophoresis is a technology that promotes absorption of drugs by using a potential difference generated by microcurrent through a means such as a patch at an application site. Although the technology has wide application, is non-invasive and painless, there may be limitations in the application when a polarity of the drug is not sufficiently strong, and there may also be limitations in a size or depth of the application of the drug. In addition, if the applied current is too strong, side effects such as erythema, itchiness, etc. may occur.

Microneedles deliver drugs by creating holes hundreds of micrometers deep in the skin. In addition, a laser system can apply the substance for preventing the hair loss to a patient's skin by dermabrasion by a depth of about 5-10 micrometers through laser irradiation, however, it may cause pain and the erythema by irritating the skin. In addition, it has a disadvantage in that it is difficult to apply repeatedly and difficult to apply to a large area.

In view of the limitations of such a drug delivery system, there is a need for a method of increasing the viability of cells without any side effects in a non-invasive and painless manner within a short period of application time.

3. SUMMARY OF THE DISCLOSURE

It is an object of the present invention to solve all the aforementioned problems.

It is another object of the present disclosure to increase viability of one or more cells in a non-invasive and painless manner by irradiating the cells with ultrasound.

It is still another object of the present disclosure to increase the viability of the cells only by irradiating the cells with the ultrasound without using expensive drugs.

In order to accomplish objects above and characteristic effects to be described later of the present disclosure, distinctive structures of the present disclosure are described as follows.

In accordance with one aspect of the present disclosure, there is provided a method for increasing a viability of one or more cells by irradiating the cells with ultrasound, including a step of: on condition that ultrasound parameters have been preset within respective ranges, an ultrasound irradiating device positioning an ultrasonic transducer within a threshold range from epidermis of a subject and then irradiating the epidermis with the ultrasound, wherein the ultrasound parameters include pressure of the ultrasound and duty percentage of the ultrasound, wherein the pressure of the ultrasound ranges from 0.5 MPa to 1 MPa, and wherein the duty percentage of the ultrasound ranges from 1% to 5%.

As one example, the ultrasound parameters further include intensity of the ultrasound, and wherein the intensity of the ultrasound ranges from 166.7 $mW/cm^2$ to 416.7 $mW/cm^2$.

As one example, the ultrasound parameters further include frequency of the ultrasound, and wherein the frequency of the ultrasound ranges from 0.5 MHz to 4.6 MHz.

As one example, the ultrasound parameters further include total irradiation time of the ultrasound, and wherein the total irradiation time is equal to or less than ten minutes.

As one example, the cells are outer root sheath cells.

In accordance with another aspect of the present disclosure, there is provided an ultrasound irradiating device for increasing viability of one or more cells by irradiating the cells with ultrasound, including: an ultrasound transducer; and a controlling part, on condition that ultrasound parameters have been preset within respective ranges, for positioning the ultrasonic transducer within a threshold range from epidermis of a subject and then allowing the ultrasonic transducer to irradiate the epidermis with the ultrasound; and wherein the ultrasound parameters include a pressure of the ultrasound and a duty percentage of the ultrasound, wherein the pressure of the ultrasound ranges from 0.5 MPa to 1 MPa, and wherein the duty percentage of the ultrasound ranges from 1% to 5%.

As one example, the ultrasound parameters further include an intensity of the ultrasound, and wherein the intensity of the ultrasound ranges from 166.7 mW/cm$^2$ to 416.7 mW/cm$^2$.

As one example, the ultrasound parameters further include a frequency of the ultrasound, and wherein the frequency of the ultrasound ranges from 0.5 MHz to 4.6 MHz.

As one example, the ultrasound parameters further include total irradiation time of the ultrasound, and wherein the total irradiation time is equal to or less than ten minutes.

As one example, the cells are outer root sheath cells.

4. BRIEF DESCRIPTION OF THE DRAWINGS

FIGS. 3A and 3B are drawings schematically illustrating the viability of human outer root sheath cells according to concentrations of applied conventional drugs in case only the conventional drugs are applied.

FIGS. 28 to 31 are drawings schematically illustrating experimental results of gene expression when the human outer root sheath cells are irradiated with the ultrasound in accordance with one example embodiment of the present disclosure.

5. DETAILED DESCRIPTION OF THE PREFERRED EMBODIMENTS

Figure 1A:
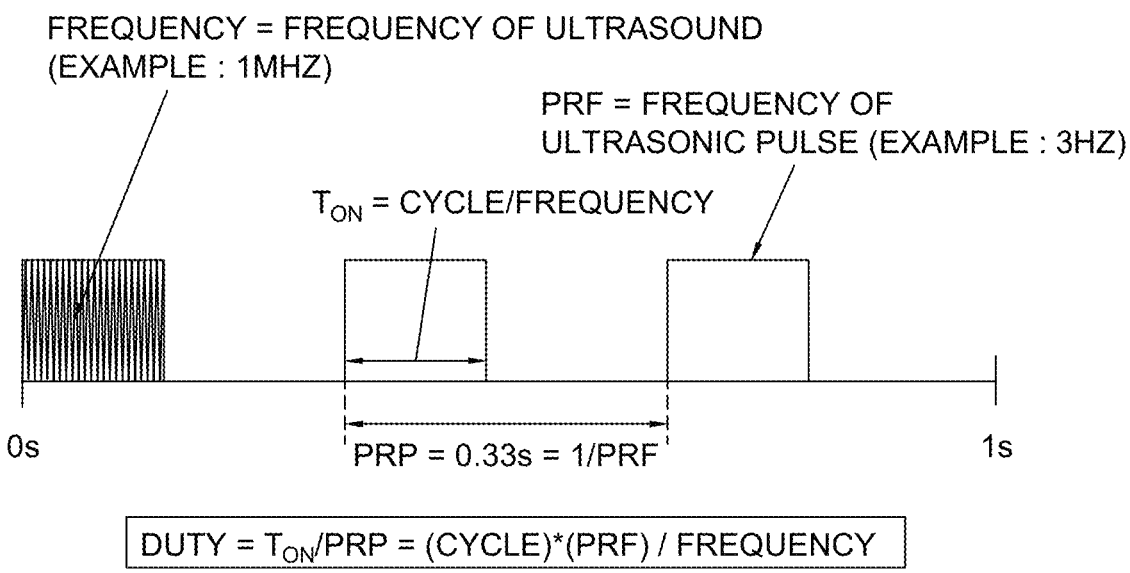
FIGS. 1A and 1B are drawings schematically illustrating ultrasound parameters used in a method for increasing viability of one or more cells by irradiating the cells with ultrasound in accordance with one example embodiment of the present disclosure.

In the following detailed description, reference is made to the accompanying drawings that show, by way of illustration, specific embodiments in which the present disclosure may be practiced. These embodiments are described in sufficient detail to enable those skilled in the art to practice the present disclosure. It is to be understood that the various embodiments of the present disclosure, although different, are not necessarily mutually exclusive. For example, a particular feature, structure, or characteristic described herein in connection with one embodiment may be implemented within other embodiments without departing from the spirit and scope of the present disclosure. In addition, it is to be understood that the position or arrangement of individual elements within each disclosed embodiment may be modified without departing from the spirit and scope of the present disclosure. The following detailed description is, therefore, not to be taken in a limiting sense, and the scope of the present disclosure is defined only by the appended claims, appropriately interpreted, along with the full range of equivalents to which the claims are entitled. In the drawings, like numerals refer to the same or similar functionality throughout the several views.

To allow those skilled in the art to carry out the present disclosure easily, the example embodiments of the present disclosure will be explained in detail by referring to attached diagrams as shown below.

Figure 1B:
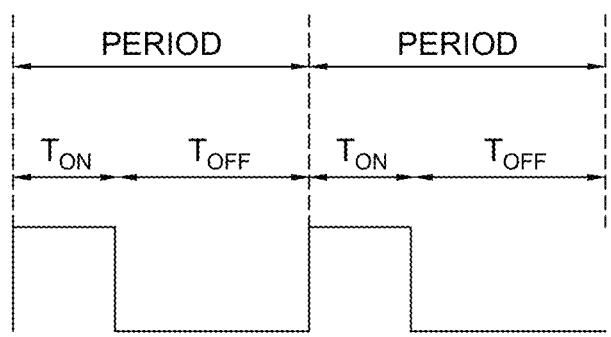

FIGS. 1A and 1B are drawings schematically illustrating ultrasound parameters used in a method for increasing viability of one or more cells by irradiating the cells with ultrasound in accordance with one example embodiment of the present disclosure.

The ultrasound parameters are as follows.

Frequency: a frequency of the ultrasound

Duty percentage: a percentage value of actual time of ultrasound irradiation divided by a period PRF (pulse repetition frequency): the number of times square wave is irradiated per second PRP (pulse repetition period): 1/PRF Pressure: a pressure of the ultrasound Intensity=(duty percentage)×pressure²/(2×c×rho): energy of the ultrasound irradiated per unit area (c: speed of sound in water=1,500 m/s, rho: density of water=1,000 kg/m³)

As an example, in FIG. 1A, the square wave of the ultrasound with the frequency of 1 MHz is repeated three times per second, thus PRF is 3 Hz and PRP, i.e., 1/PRF, is 0.3333 second. Herein, a cycle may be a time between an instantaneous peak and its neighboring instantaneous peak in an envelope. Also, in FIG. 1B, the duty percentage is Ton/(Ton+Toff)×100, i.e., a time Ton, during which the actual ultrasound is irradiated, divided by the period Ton+Toff of the ultrasound irradiation.

For reference, a Table 1 below describes intensities according to pressures and duty percentages of the ultrasound.

TABLE 1

| Pressure (MPa) | Intensity (W/m²) | Intensity with 100% duty percentage (W/cm²) | Intensity with 1% duty percentage (mW/cm²) | Intensity with 2% duty percentage (mW/cm²) | Intensity with 3% duty percentage (mW/cm²) | Intensity with 5% duty percentage (mW/cm²) |
| --- | --- | --- | --- | --- | --- | --- |
| 0.5 | 83333.3 | 8.3 | 83.3 | 166.7 | 250.0 | 416.7 |
| 0.7 | 163333.3 | 16.3 | 163.3 | 326.7 | 490.0 | 816.7 |
| 1 | 333333.3 | 33.3 | 333.3 | 666.7 | 1000.0 | 1666.7 |

Figure 2:
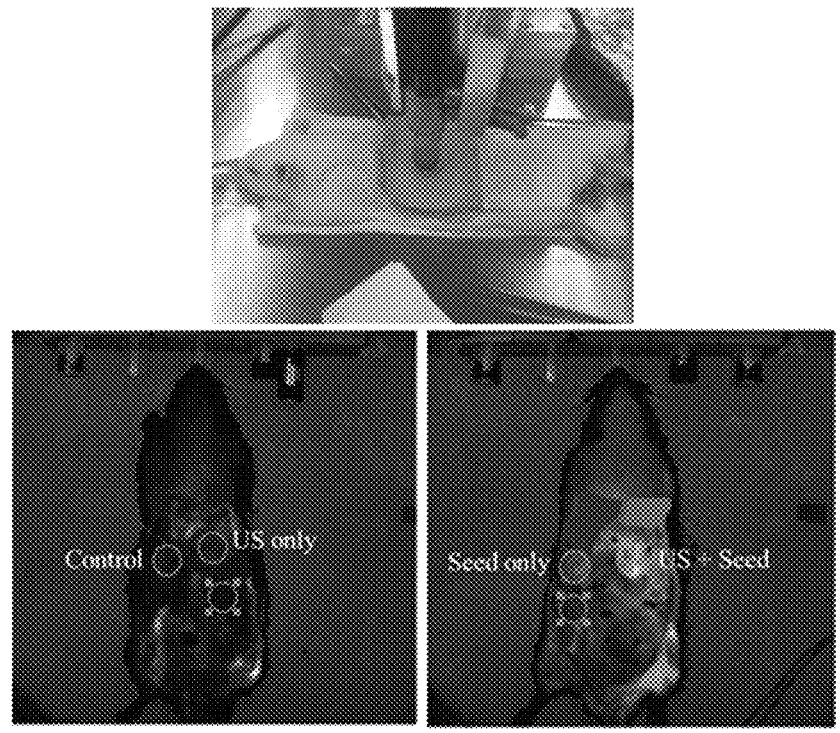
FIG. 2 is a drawing schematically illustrating experimental results of a dermal stability of the method for increasing the viability of the cells by irradiating the cells with the ultrasound in accordance with one example embodiment of the present disclosure.

Next, FIG. 2 is a drawing schematically illustrating experimental results of a dermal stability of the method for increasing the viability of the cells by irradiating the cells with the ultrasound in accordance with one example embodiment of the present disclosure.

Specifically, as a result of monitoring temperature changes during the ultrasound irradiation on a skin of an 8-week-old male rat, it is observed that a skin temperature increased by about 1.2 degrees Celsius after 30 minutes and that 0.05 degrees Celsius per minute was changed in temperature on average. That is, it can be seen that the degree of temperature change due to the ultrasound irradiation does not reach as much extent as it damages the skin.

Next, experimental conditions for observing the viability of the cells according to the ultrasound irradiation are described.

For reference, a Table 2 below describes cell seeding densities.

TABLE 2

| Recommended seeding density | 5 * 10³ cells/cm² | |
| --- | --- | --- |
| Dish | Surface area (cm²) | Seeding density |
| 60 mm | 21 | 1.05 * 10⁵ cells |
| 100 mm | 55 | 2.75 * 10⁵ cells |
| T75 | 75 | 3.75 * 10⁵ cells |

Also, a Table 3 below describes required amounts of the cells according to the conditions.

TABLE 3

| | | Ultrasound is irradiated per well for 10 minutes | Number of wells | Number of cells seeding (total amount) | T75 flask |
|---|---|---|---|---|---|
| Cell viability assay | 96 well plate($3 * 10^3$ cell/well) | Condition 3 wells | 22 66 | $6.6 * 10^4$ $1.98 * 10^5$ | $8.4 * 10^6$ |
| | 6 well plate($8 * 10^4$ cell/well) | Condition 3 wells | 20 60 | $1.6 \times 10^6$ $4.8 \times 10^6$ | |
| PCR | 6 well plate | Condition for drug Condition for ultrasound 3 wells | 22 20 126 | $1.76 \times 10^6$ $1.6 \times 10^6$ $1 \times 10^7$ | |

First, to explain the material, a cell culture is comprised of human hair outer root sheath cells (HHORSC), a mesenchymal stem cell medium (MSCM), an FBS 0.25% trypsin/EDTA solution, a trypsin neutralization solution, a Dulbecco's phosphate-buffered saline (DPBS), and poly-L-lysine.

And a WST-1 cell proliferation assay system is used for WST-1 assay. Further, Trizol, a sensiFAST probe Hi-ROX one step kit, PrimeTime qPCR assay are used for PCR.

First, for culture dish coating (based on a T75 flask), 10 mL of deionized water (D.W.) is put into the T75 flask and then 15 μL of poly-L-lysine (10 mg/mL) is put into the T75 flask. Then, the T75 flask is placed in an incubator at 37° C. and an inside of the T75 flask is coated with poly-L-lysine for 1 hour. And the T75 flask is washed twice with D.W.

And a whole medium is created by using MSCM consisting of 500 mL basal medium, 25 mL FBS, and 5 mL of mesenchymal stem cells.

And, a frozen cell vial is warmed in a water bath at 37° C. Then the melted cells are placed on a growth medium of 3 mL and centrifuged at 3,000 rpm for 3 minutes to pull the cells down to the bottom. Then, DPBS is added to the centrifuged cells, and after washing, centrifuged again at 3,000 rpm for 3 minutes to pull the cells down, and these processes are repeated twice, creating cell pellets. Then, 8 mL of the growth medium is put into the T75 flask coated with poly-L-lysine, the cell pellets are dissolved therein, and after seeding, the T75 flask is placed in an incubator at 37° C. with 5% $CO_2$.

And, if it is confirmed under the microscope that the cells have grown more than 90% in the cell subculture of the T75 flask, (i) 3 mL of DPBS is added to the cell subculture and washed and (ii) 3 mL of the trypsin/EDTA solution is added and the T75 flask is placed in the incubator at 37° C. for 3 minutes. Then, if it is confirmed that the cells have fallen from the T75 flask, (i) each 3 mL of the growth medium and the trypsin neutralization solution is added to the T75 flask in order to neutralize the trypsin/EDTA solution, (ii) the neutralized cell solution is transferred to a conical tube, and centrifuged at 3,000 rpm for 3 minutes to pull the cells down, creating cell pellets, (iii) 8 mL of the growth medium is put into the T75 flask coated with poly-L-lysine, (iv) the cell pellets are dissolved in the T75 flask, and (v) after seeding, the T75 flask is placed in the incubator at 37° C. with 5% $CO_2$.

And, for 6 well plate/96 well plate cell seeding, poly-L-lysine is added for each plate according to a Table 4 below, and poly-L-lysine coating is performed according to a culture dish coating procedure.

TABLE 4

Required amount of poly-L-lysine per surface area (μg/cm$^2$)

| Dish | Surface area (cm$^2$) | Required amount of poly-L-lysine (μg) | 2 Poly-L-lysine (μL) of 10 mg/mL |
|---|---|---|---|
| T75 | 75 | 150 | 15 |
| 100 mm | 55 | 110 | 11 |
| 6 wells | 4.8 | 9.6 | 2 |
| 12 wells | 3.9 | 7.8 | 0.78 (7.8 μL as a result of 1/10 dilution) |
| 96 wells | 0.3 | 0.6 | 0.06 (6 μL as a result of 1/100 dilution) |

Herein, if it is confirmed under the microscope that the cells have grown more than 90% in the cell subculture of the T75 flask, (i) 3 mL of DPBS is added to the cell subculture and washed and (ii) 3 mL of the trypsin/EDTA solution is added and the T75 flask is placed in the incubator at 37° C. for 3 minutes. Then, if it is confirmed that the cells have fallen from the T75 flask, (i) each 3 mL of the growth medium and the trypsin neutralization solution is added to the T75 flask in order to neutralize the trypsin/EDTA solution, (ii) the neutralized cell solution is transferred to the conical tube, and centrifuged at 3,000 rpm for 3 minutes to pull the cells down, and (iii) the cells are counted using trypan blue and a hemocytometer. And the cells are seeded as many as $8\times10^4$ in the 6 well plate and $4\times10^4$ in the 96 well plate.

For WST assay, in a case of an experiment of the ultrasound irradiation only, the cells seeded in the 6 well plate are cultured for 12 to 18 hours and observed with the microscope. And after removing the medium, the cells are washed twice with DPBS, put into a growth factor free medium, and irradiated with the ultrasound for 10 minutes. Then, the 6 well plate is placed in the incubator at 37° C. with 5% $CO_2$ and incubated for 24 hours, then the medium is removed therefrom. The 6 well plate is then washed with DPBS, treated with 0.2 mL of WST-1, and placed in the incubator for 3 hours. Then supernatant is transferred from each well of the 6 well plate into 3 wells of a 96 well plate, and the 96 well plate is measured with a microplate reader at 450 nm.

For the WST assay, in a case of an experiment with drugs only, the cells seeded in the 96 well plate are cultured for 12 to 18 hours and confirmed whether the cells are seeded sufficiently. And after removing the medium, the cells are washed twice with DPBS, put into the growth factor free medium, and a drug is applied to the cells. Then, the 96 well plate is placed in the incubator at 37° C. with 5% $CO_2$ for 24 hours, then the medium is removed therefrom. The 96 well plate is then washed with DPBS, treated with 0.2 mL of WST-1, and placed in the incubator for 3 hours. Then the 96 well plate is measured with the microplate reader at 450 nm.

Meanwhile, FIGS. 3A and 3B are drawings schematically illustrating the viability of the human outer root sheath cells according to concentrations of applied conventional drugs in case only the conventional drugs are applied.

Specifically, FIG. 3A shows the viability of the cells according to the concentrations of applied Redensyl, i.e., a hair loss treatment drug, and FIG. 3B shows the viability of the cells according to the concentrations of applied minoxidil, i.e., another hair loss treatment drug.

For reference, a Table 5 below shows experimental conditions when the drugs are applied only. Herein, a solubility of minoxidil is 0.2% in PBS, on a condition of being measured 24 hours after application of the drug.

TABLE 5

| | 96 well plate | | |
|---|---|---|---|
| Control | Positive control (EGF) | Minoxidil | Redensyl |
| Medium | 50 ng/100 μL | 0.00002% | 0.01% |
| | | 0.0002% | 0.02% |
| | | 0.002% | 0.04% |
| | | 0.05% | 0.1% |
| | | 0.01% | 0.2% |
| | | 0.02% | 0.5% |
| | | 0.05% | 1% |
| | | 0.15% | 2% |
| | | 0.2% | 3% |
| | | | 4% |
| | | | 5% |
| | | | 10% |

Figure 4:
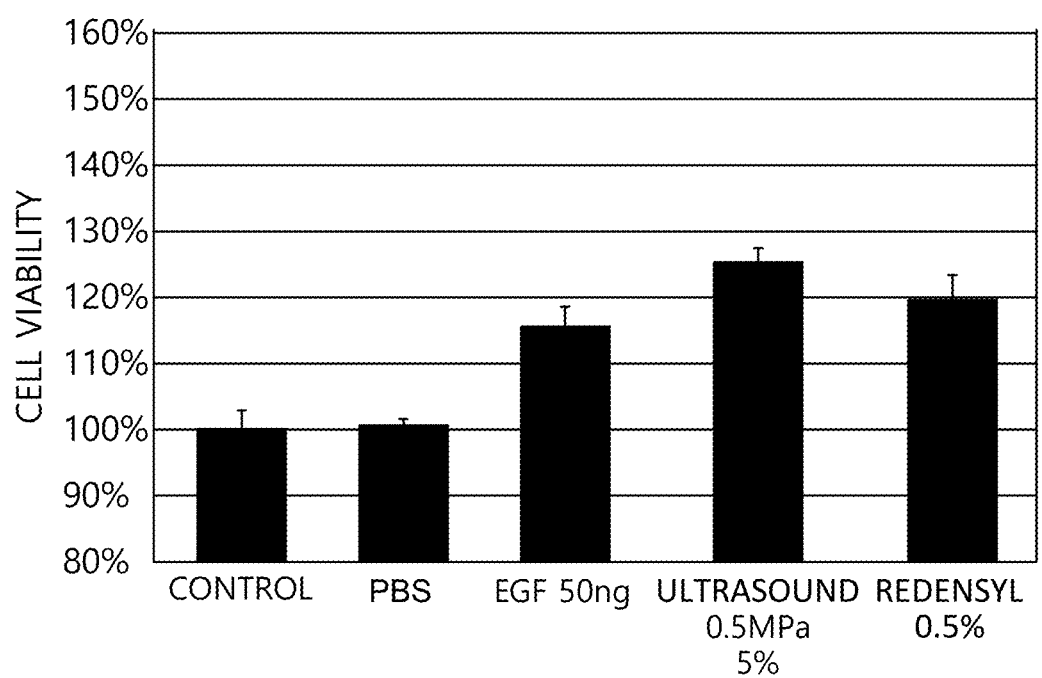
FIG. 4 is a drawing schematically illustrating experimental results of the viability of the human outer root sheath cells by using some of the conventional drugs and the experimental results of the method for increasing the viability of the cells by irradiating the cells with the ultrasound in accordance with one example embodiment of the present disclosure.

Next, FIG. 4 is a drawing schematically illustrating experimental results of the viability of the human outer root sheath cells by using some of the conventional drugs and the experimental results of the method for increasing the viability of the cells by irradiating the cells with the ultrasound in accordance with one example embodiment of the present disclosure.

By referring to FIG. 4, when compared with cases of (i) 50 ng administration of EGF and (ii) application of Redensyl having a concentration of 0.5%, a higher cell viability is shown in the case of irradiating the ultrasound only (pressure: 0.5 MPa and duty percentage: 5%) without applying any drugs.

Meanwhile, in the cell experiment, a comparison between MTT and WST-1 was performed, and in the case of MTT, there was a problem of overlapping between an absorbance range of Redensyl and an absorbance range of MTT, resulting in a poor data accuracy. On the other hand, in the case of WST-1, since the absorbance range of Redensyl and the absorbance range of WST-1 did not overlap each other, the experiment was conducted by using WST-1.

In addition, a media comparison was performed. In a first experiment, after seeding stabilization, complete media was treated with Redensyl and observed for 24 hours. However, a time duration is not limited to 24 hours, and may be changed according to cell conditions. Also, in a second experiment, after the seeding stabilization, the media without a growth factor were treated with Redensyl and observed for 24 hours. Like the first experiment, the time duration of the second experiment may be changed according to the cell conditions.

By referring to the first experiment and the second experiment, an effect of the ultrasound was better observed when the media did not contain the growth factor. Therefore, the experiment was conducted by treating the media, which did not contain the growth factor, with Redensyl.

Subsequently, the ultrasound irradiation was conducted, and a quantitative analysis was performed through an assay before and after the ultrasound irradiation.

Tables 6 to 9 describe the experimental conditions of the ultrasound irradiation for evaluating physical effects of the ultrasound on the cells.

Specifically, Tables 6 and 7 describe observation conditions of Redensyl treatment on serum free media and complete media left overnight during the stabilization after the seeding.

TABLE 6

| 96Well-1 | A | B | C | D | E | F | G | H |
|---|---|---|---|---|---|---|---|---|
| 1 | M-24-XTT | M-24-XTT | M-24-XTT | M-24-XTT | M-24-XTT | M-24-XTT | M-24-XTT | M-24-XTT |
| 2 | P-24-XTT | P-24-XTT | P-24-XTT | P-24-XTT | P-24-XTT | P-24-XTT | P-24-XTT | P-24-XTT |
| 3 | R0.01-24-XTT | R0.01-24-XTT | R0.01-24-XTT | R0.01-24-XTT | R0.01-24-XTT | R0.01-24-XTT | R0.01-24-XTT | R0.01-24-XTT |
| 4 | R0.04-24-XTT | R0.04-24-XTT | R0.04-24-XTT | R0.04-24-XTT | R0.04-24-XTT | R0.04-24-XTT | R0.04-24-XTT | R0.04-24-XTT |
| 5 | R0.2-24-XTT | R0.2-24-XTT | R0.2-24-XTT | R0.2-24-XTT | R0.2-24-XTT | R0.2-24-XTT | R0.2-24-XTT | R0.2-24-XTT |
| 6 | R1-24-XTT | R1-24-XTT | R1-24-XTT | R1-24-XTT | R1-24-XTT | R1-24-XTT | R1-24-XTT | R1-24-XTT |
| 7 | M-24-WST | M-24-WST | M-24-WST | M-24-WST | M-24-WST | M-24-WST | M-24-WST | M-24-WST |
| 8 | P-24-WST | P-24-WST | P-24-WST | P-24-WST | P-24-WST | P-24-WST | P-24-WST | P-24-WST |
| 9 | R0.01-24-WST | R0.01-24-WST | R0.01-24-WST | R0.01-24-WST | R0.01-24-WST | R0.01-24-WST | R0.01-24-WST | R0.01-24-WST |
| 10 | R0.04-24-WST | R0.04-24-WST | R0.04-24-WST | R0.04-24-WST | R0.04-24-WST | R0.04-24-WST | R0.04-24-WST | R0.04-24-WST |
| 11 | R0.2-24-WST | R0.2-24-WST | R0.2-24-WST | R0.2-24-WST | R0.2-24-WST | R0.2-24-WST | R0.2-24-WST | R0.2-24-WST |
| 12 | R1-24-WST | R1-24-WST | R1-24-WST | R1-24-WST | R1-24-WST | R1-24-WST | R1-24-WST | R1-24-WST |

TABLE 7

| 96Well-2 | A | B | C | D | E | F | G | H |
|---|---|---|---|---|---|---|---|---|
| 1 | M-48-XTT | M-48-XTT | M-48-XTT | M-48-XTT | M-48-XTT | M-48-XTT | M-48-XTT | M-48-XTT |
| 2 | P-48-XTT | P-48-XTT | P-48-XTT | P-48-XTT | P-48-XTT | P-48-XTT | P-48-XTT | P-48-XTT |
| 3 | R0.01-48-XTT | R0.01-48-XTT | R0.01-48-XTT | R0.01-48-XTT | R0.01-48-XTT | R0.01-48-XTT | R0.01-48-XTT | R0.01-48-XTT |
| 4 | R0.04-48-XTT | R0.04-48-XTT | R0.04-48-XTT | R0.04-48-XTT | R0.04-48-XTT | R0.04-48-XTT | R0.04-48-XTT | R0.04-48-XTT |
| 5 | R0.2-48-XTT | R0.2-48-XTT | R0.2-48-XTT | R0.2-48-XTT | R0.2-48-XTT | R0.2-48-XTT | R0.2-48-XTT | R0.2-48-XTT |
| 6 | R1-48-XTT | R1-48-XTT | R1-48-XTT | R1-48-XTT | R1-48-XTT | R1-48-XTT | R1-48-XTT | R1-48-XTT |

TABLE 7-continued

| 96Well-2 | A | B | C | D | E | F | G | H |
|---|---|---|---|---|---|---|---|---|
| 7 | M-48-WST | M-48-WST | M-48-WST | M-48-WST | M-48-WST | M-48-WST | M-48-WST | M-48-WST |
| 8 | P-48-WST | P-48-WST | P-48-WST | P-48-WST | P-48-WST | P-48-WST | P-48-WST | P-48-WST |
| 9 | R0.01-48-WST | R0.01-48-WST | R0.01-48-WST | R0.01-48-WST | R0.01-48-WST | R0.01-48-WST | R0.01-48-WST | R0.01-48-WST |
| 10 | R0.04-48-WST | R0.04-48-WST | R0.04-48-WST | R0.04-48-WST | R0.04-48-WST | R0.04-48-WST | R0.04-48-WST | R0.04-48-WST |
| 11 | R0.2-48-WST | R0.2-48-WST | R0.2-48-WST | R0.2-48-WST | R0.2-48-WST | R0.2-48-WST | R0.2-48-WST | R0.2-48-WST |
| 12 | R1-48-WST | R1-48-WST | R1-48-WST | R1-48-WST | R1-48-WST | R1-48-WST | R1-48-WST | R1-48-WST |

In addition, Tables 8 and 9 describe the conditions of Redensyl treatment on the serum free media after the seeding and the stabilization.

TABLE 8

| 96Well-3 | A | B | C | D | E | F | G | H |
|---|---|---|---|---|---|---|---|---|
| 1 | M-24-XTT | M-24-XTT | M-24-XTT | M-24-XTT | M-24-XTT | M-24-XTT | M-24-XTT | M-24-XTT |
| 2 | P-24-XTT | P-24-XTT | P-24-XTT | P-24-XTT | P-24-XTT | P-24-XTT | P-24-XTT | P-24-XTT |
| 3 | R0.01-24-XTT | R0.01-24-XTT | R0.01-24-XTT | R0.01-24-XTT | R0.01-24-XTT | R0.01-24-XTT | R0.01-24-XTT | R0.01-24-XTT |
| 4 | R0.04-24-XTT | R0.04-24-XTT | R0.04-24-XTT | R0.04-24-XTT | R0.04-24-XTT | R0.04-24-XTT | R0.04-24-XTT | R0.04-24-XTT |
| 5 | R0.2-24-XTT | R0.2-24-XTT | R0.2-24-XTT | R0.2-24-XTT | R0.2-24-XTT | R0.2-24-XTT | R0.2-24-XTT | R0.2-24-XTT |
| 6 | R1-24-XTT | R1-24-XTT | R1-24-XTT | R1-24-XTT | R1-24-XTT | R1-24-XTT | R1-24-XTT | R1-24-XTT |
| 7 | M-24-WST | M-24-WST | M-24-WST | M-24-WST | M-24-WST | M-24-WST | M-24-WST | M-24-WST |
| 8 | P-24-WST | P-24-WST | P-24-WST | P-24-WST | P-24-WST | P-24-WST | P-24-WST | P-24-WST |
| 9 | R0.01-24-WST | R0.01-24-WST | R0.01-24-WST | R0.01-24-WST | R0.01-24-WST | R0.01-24-WST | R0.01-24-WST | R0.01-24-WST |
| 10 | R0.04-24-WST | R0.04-24-WST | R0.04-24-WST | R0.04-24-WST | R0.04-24-WST | R0.04-24-WST | R0.04-24-WST | R0.04-24-WST |
| 11 | R0.2-24-WST | R0.2-24-WST | R0.2-24-WST | R0.2-24-WST | R0.2-24-WST | R0.2-24-WST | R0.2-24-WST | R0.2-24-WST |
| 12 | R1-24-WST | R1-24-WST | R1-24-WST | R1-24-WST | R1-24-WST | R1-24-WST | R1-24-WST | R1-24-WST |

TABLE 9

| 96Well-4 | A | B | C | D | E | F | G | H |
|---|---|---|---|---|---|---|---|---|
| 1 | M-48-XTT | M-48-XTT | M-48-XTT | M-48-XTT | M-48-XTT | M-48-XTT | M-48-XTT | M-48-XTT |
| 2 | P-48-XTT | P-48-XTT | P-48-XTT | P-48-XTT | P-48-XTT | P-48-XTT | P-48-XTT | P-48-XTT |
| 3 | R0.01-48-XTT | R0.01-48-XTT | R0.01-48-XTT | R0.01-48-XTT | R0.01-48-XTT | R0.01-48-XTT | R0.01-48-XTT | R0.01-48-XTT |
| 4 | R0.04-48-XTT | R0.04-48-XTT | R0.04-48-XTT | R0.04-48-XTT | R0.04-48-XTT | R0.04-48-XTT | R0.04-48-XTT | R0.04-48-XTT |
| 5 | R0.2-48-XTT | R0.2-48-XTT | R0.2-48-XTT | R0.2-48-XTT | R0.2-48-XTT | R0.2-48-XTT | R0.2-48-XTT | R0.2-48-XTT |
| 6 | R1-48-XTT | R1-48-XTT | R1-48-XTT | R1-48-XTT | R1-48-XTT | R1-48-XTT | R1-48-XTT | R1-48-XTT |
| 7 | M-48-WST | M-48-WST | M-48-WST | M-48-WST | M-48-WST | M-48-WST | M-48-WST | M-48-WST |
| 8 | P-48-WST | P-48-WST | P-48-WST | P-48-WST | P-48-WST | P-48-WST | P-48-WST | P-48-WST |
| 9 | R0.01-48-WST | R0.01-48-WST | R0.01-48-WST | R0.01-48-WST | R0.01-48-WST | R0.01-48-WST | R0.01-48-WST | R0.01-48-WST |
| 10 | R0.04-48-WST | R0.04-48-WST | R0.04-48-WST | R0.04-48-WST | R0.04-48-WST | R0.04-48-WST | R0.04-48-WST | R0.04-48-WST |
| 11 | R0.2-48-WST | R0.2-48-WST | R0.2-48-WST | R0.2-48-WST | R0.2-48-WST | R0.2-48-WST | R0.2-48-WST | R0.2-48-WST |
| 12 | R1-48-WST | R1-48-WST | R1-48-WST | R1-48-WST | R1-48-WST | R1-48-WST | R1-48-WST | R1-48-WST |

Also, a Table 10 describes the experimental conditions for irradiating the ultrasound while varying the pressure and the duty percentage of the ultrasound.

TABLE 10

| | 1 | 2 | 3 |
|---|---|---|---|
| 6Well-1 | | | |
| A | 1 MPa, 3% | 1 MPa, 2% | 1 MPa, 1% |
| B | 0.5 MPa, 3% | 0.5 MPa, 2% | 0.5 MPa, 1% |
| 6Well-2 | | | |
| A | 1 MPa, 3% | 1 MPa, 2% | 1 MPa, 1% |
| B | 0.5 MPa, 3% | 0.5 MPa, 2% | 0.5 MPa, 1% |
| 6Well-3 | | | |
| A | 1 MPa, 3% | 1 MPa, 2% | 1 MPa, 1% |
| B | 0.5 MPa, 3% | 0.5 MPa, 2% | 0.5 MPa, 1% |
| 6Well-4 | | | |
| A | Control | Control | Control |
| B | 1.5 MPa, 10% | 1.5 MPa, 5% | |
| 6Well-5 | | | |
| A | | | |
| B | | | |
| 6Well-6 | | | |
| A | | | |
| B | | | |

By referring to the Table 10, while varying the pressure (0.5 MPa, 1 MPa, and 1.5 MPa) and the duty percentage (1%, 2%, and 3%) of the ultrasound, the experiment was performed in which the cells were irradiated with the ultrasound for 10 minutes.

Specifically, in the wells No. 1 to No. 3, the ultrasound with the pressure of 0.5 MPa or 1 MPa, and the duty percentage of 1% to 3% is used.

However, in the well No. 4, the higher pressure (1.5 MPa) and the higher duty percentage (5% and 10%) were used for inducing cell death in order to compare the results of other pressures and other duty percentages with the results thereof.

The results are shown in FIGS. 5 to 21.

Figure 5:
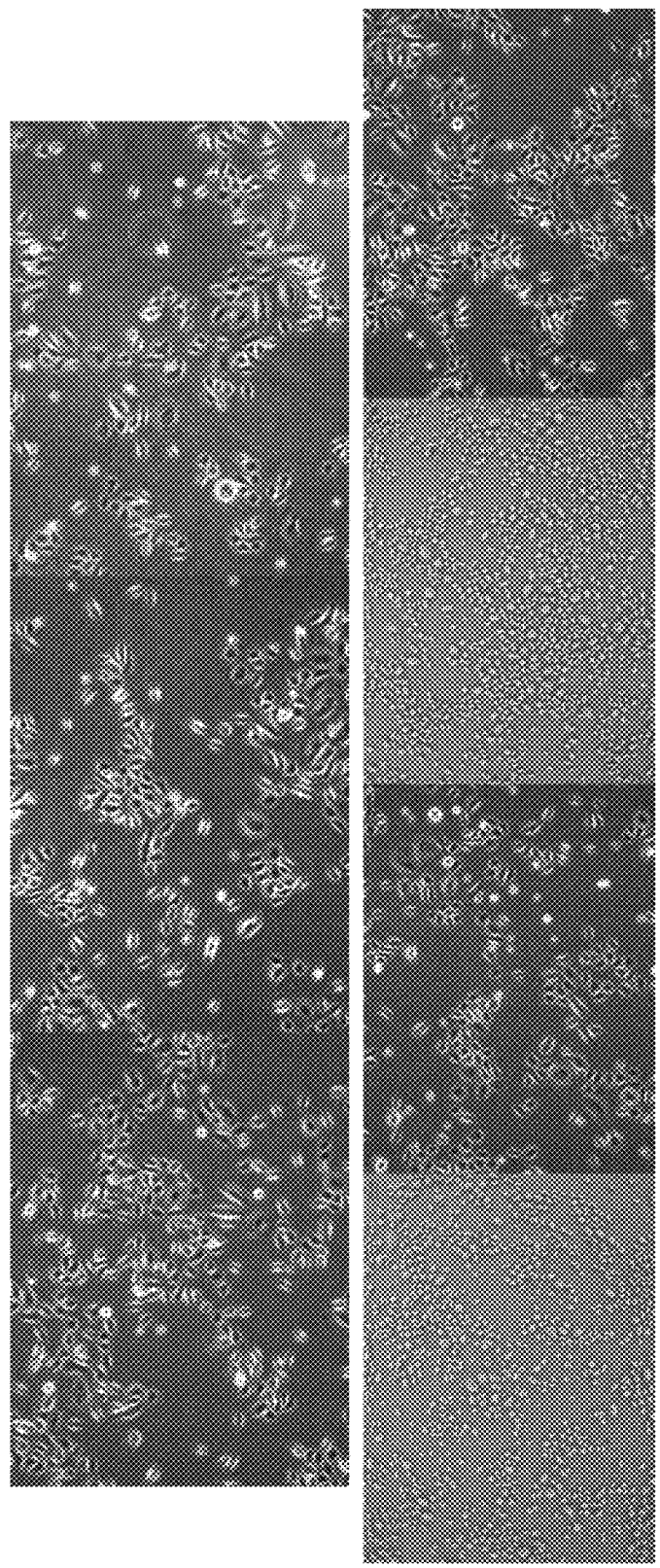
FIG. 5 is a drawing schematically illustrating experimental results of the viability of the human outer root sheath cells in a control group.

First, FIG. 5 shows the viability of the human outer root sheath cells at a specific point of time and the viability of the human outer root sheath cells after 12 hours from the specific point of time, wherein the human outer root sheath cells are not irradiated with the ultrasound, serving as the control group to be used for comparison with an experiment group with which the ultrasound is irradiated.

By referring to FIG. 5, if the human outer root sheath cells are not irradiated with the ultrasound then no significant changes are observed in the viability after 12 hours from the specific point of time represented in drawings shown on a right side, compared to the viability at the specific point of time represented in drawings shown on a left side.

Figure 6:
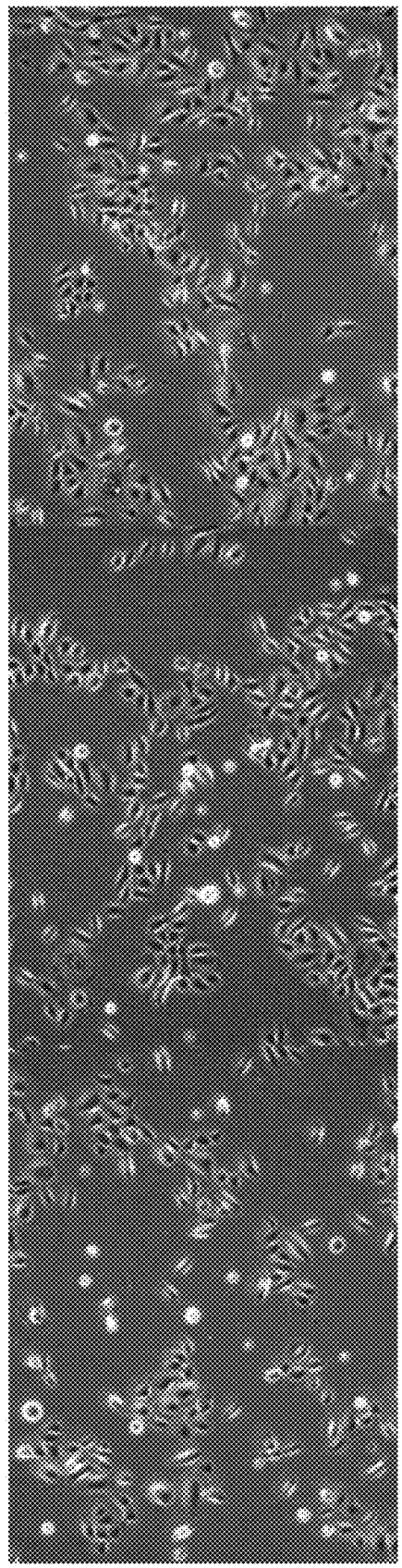
FIG. 6 is a drawing schematically illustrating experimental results right after the human outer root sheath cells are irradiated with the ultrasound having a pressure of 0.5 MPa and a duty percentage of 1% in accordance with one example embodiment of the present disclosure.

FIG. 6 is a drawing schematically illustrating experimental results right after the human outer root sheath cells are irradiated with the ultrasound (the pressure: 0.5 MPa and the duty percentage: 1%) in accordance with one example embodiment of the present disclosure.

Figure 7:
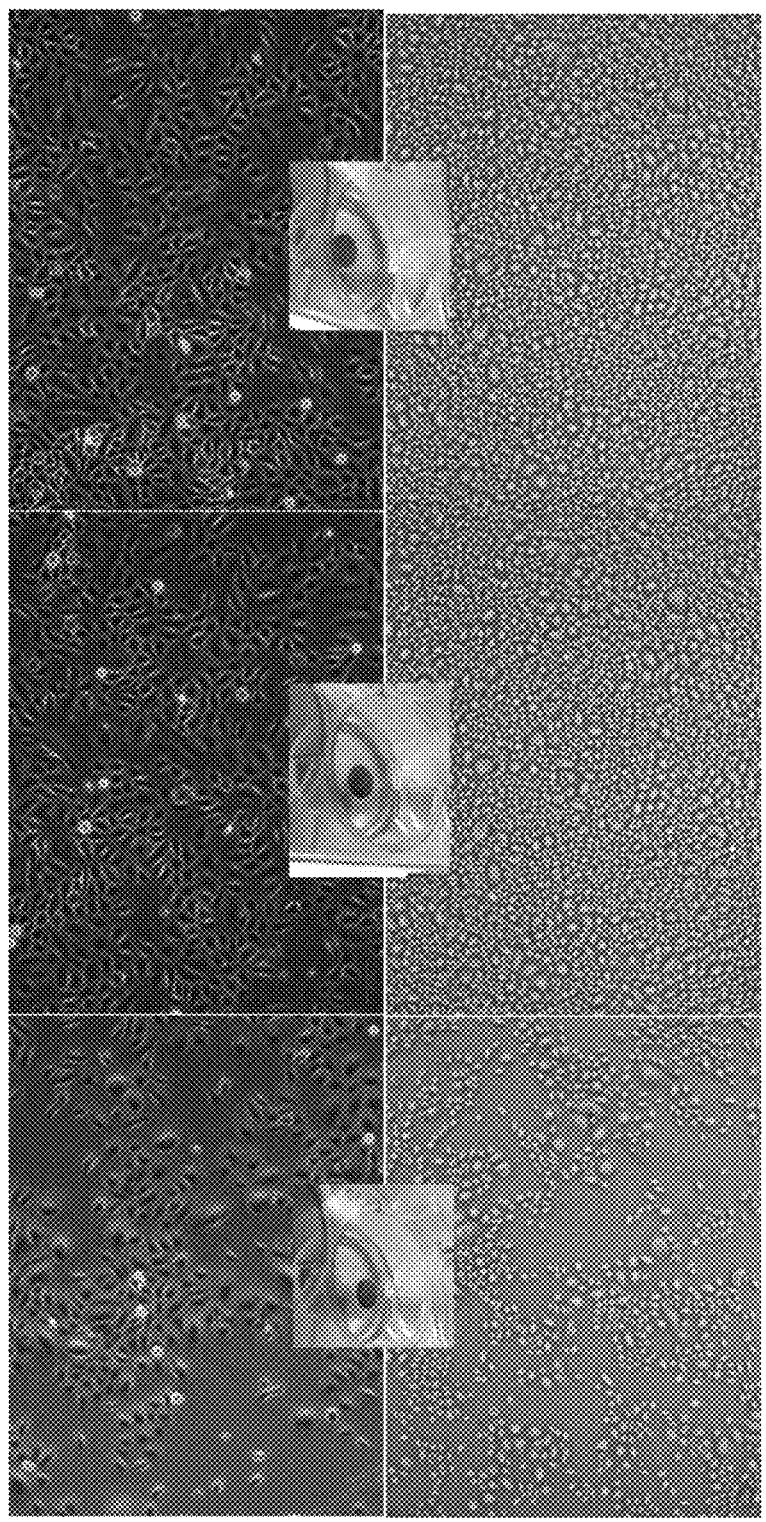
FIG. 7 is a drawing schematically illustrating experimental results 12 hours after the human outer root sheath cells are irradiated with the ultrasound having the pressure of 0.5 MPa and the duty percentage of 1% in accordance with one example embodiment of the present disclosure.

FIG. 7 is a drawing schematically illustrating experimental results 12 hours after the human outer root sheath cells are irradiated with the ultrasound (the pressure: 0.5 MPa and the duty percentage: 1%) in accordance with one example embodiment of the present disclosure.

By referring to FIGS. 6 and 7, compared to the results of the control group after 12 hours, an increase to some extent is observed in the viability of the cells 12 hours after the cells are irradiated with the ultrasound (the pressure: 0.5 MPa and the duty percentage: 1%).

Figure 8:
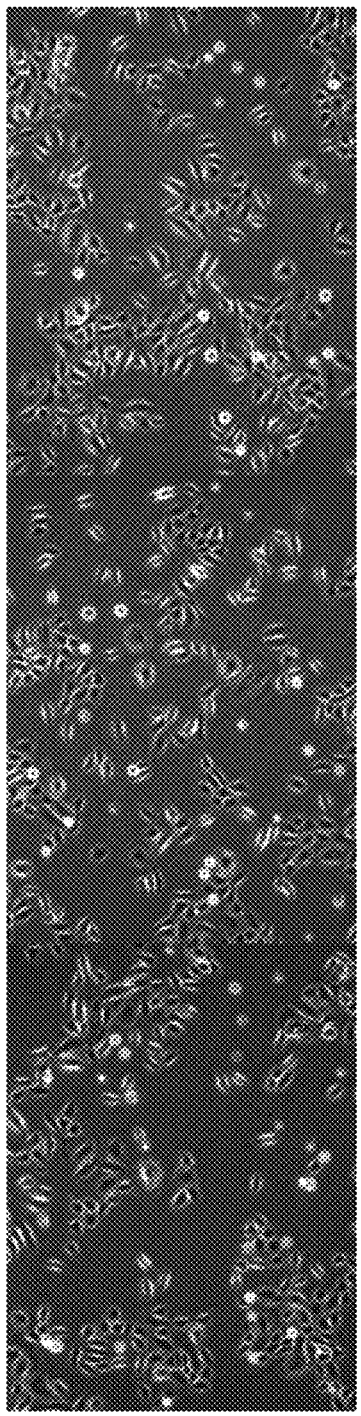
FIG. 8 is a drawing schematically illustrating experimental results right after the human outer root sheath cells are irradiated with the ultrasound having the pressure of 0.5 MPa and the duty percentage of 2% in accordance with one example embodiment of the present disclosure.

FIG. 8 is a drawing schematically illustrating experimental results right after the human outer root sheath cells are irradiated with the ultrasound (the pressure: 0.5 MPa and the duty percentage: 2%) in accordance with one example embodiment of the present disclosure.

Figure 9:
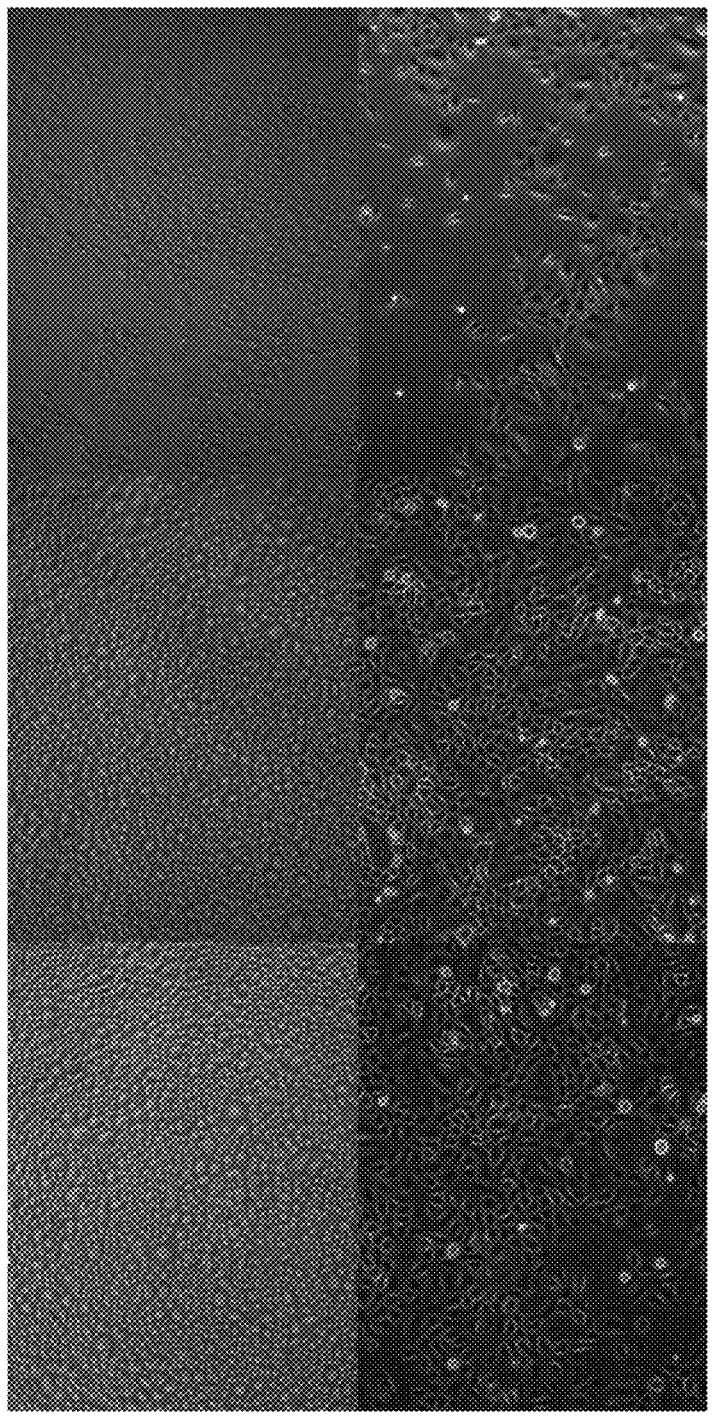
FIG. 9 is a drawing schematically illustrating experimental results 12 hours after the human outer root sheath cells are irradiated with the ultrasound having the pressure of 0.5 MPa and the duty percentage of 2% in accordance with one example embodiment of the present disclosure.

FIG. 9 is a drawing schematically illustrating experimental results 12 hours after the human outer root sheath cells are irradiated with the ultrasound (the pressure: 0.5 MPa and the duty percentage: 2%) in accordance with one example embodiment of the present disclosure.

By referring to FIGS. 8 and 9, compared to the results of the control group after 12 hours, a significant increase is observed in the viability of the cells 12 hours after the cells are irradiated with the ultrasound (the pressure: 0.5 MPa and the duty percentage: 2%).

Figure 10:
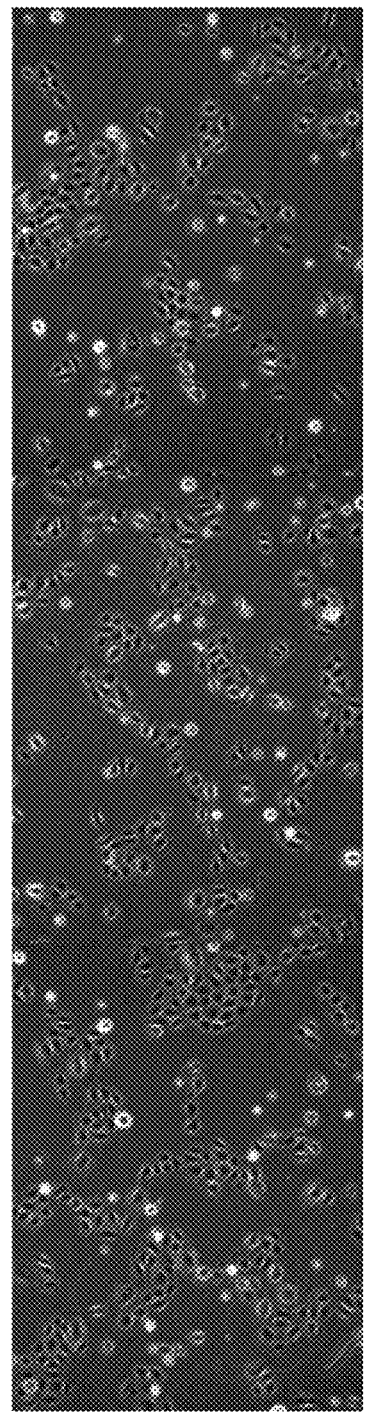
FIG. 10 is a drawing schematically illustrating experimental results right after the human outer root sheath cells are irradiated with the ultrasound having the pressure of 0.5 MPa and the duty percentage of 3% in accordance with one example embodiment of the present disclosure.

FIG. 10 is a drawing schematically illustrating experimental results right after the human outer root sheath cells are irradiated with the ultrasound (the pressure: 0.5 MPa and the duty percentage: 3%) in accordance with one example embodiment of the present disclosure.

Figure 11:
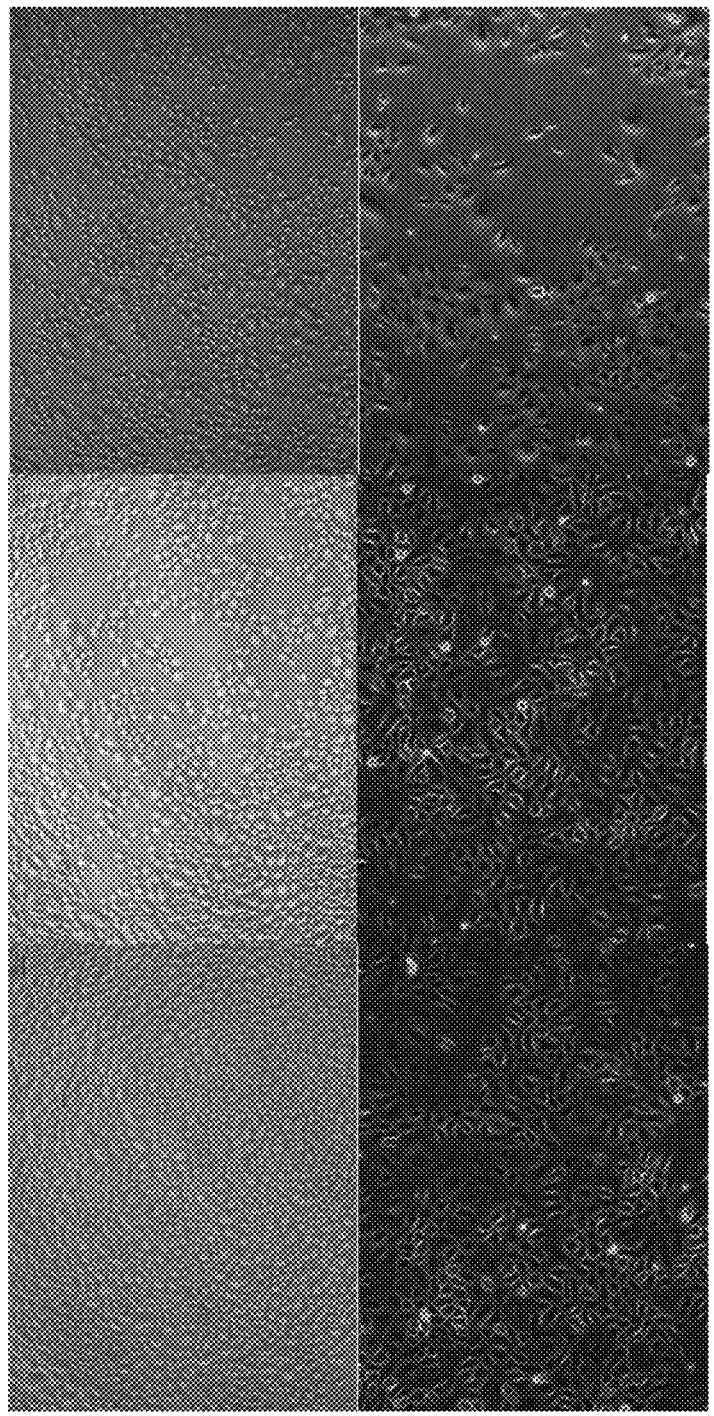
FIG. 11 is a drawing schematically illustrating experimental results 12 hours after the human outer root sheath cells are irradiated with the ultrasound having the pressure of 0.5 MPa and the duty percentage of 3% in accordance with one example embodiment of the present disclosure.

FIG. 11 is a drawing schematically illustrating experimental results 12 hours after the human outer root sheath cells are irradiated with the ultrasound (the pressure: 0.5 MPa and the duty percentage: 3%) in accordance with one example embodiment of the present disclosure.

By referring to FIGS. 10 and 11, compared to the results of the control group after 12 hours, a significant increase is observed in the viability of the cells 12 hours after the cells are irradiated with the ultrasound (the pressure: 0.5 MPa and the duty percentage: 3%).

Figure 12:
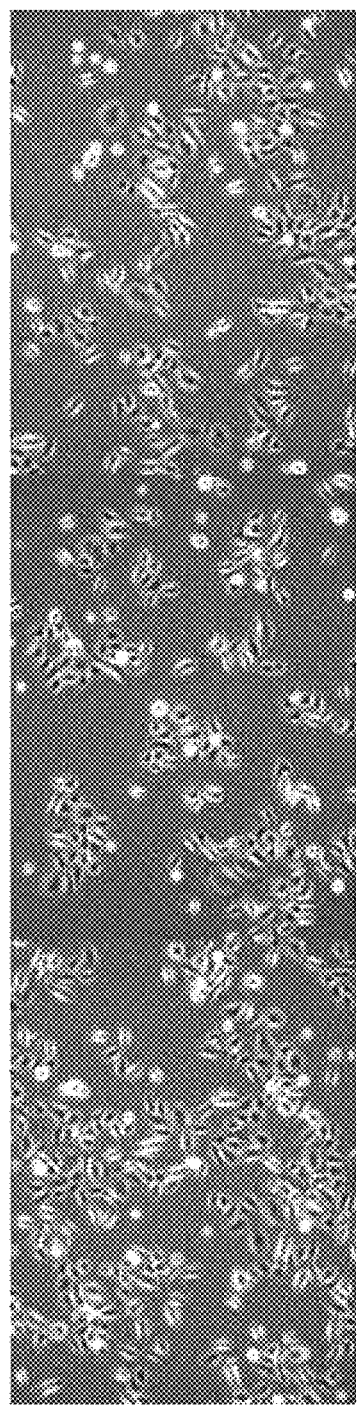
FIG. 12 is a drawing schematically illustrating experimental results right after the human outer root sheath cells are irradiated with the ultrasound having the pressure of 1 MPa and the duty percentage of 1% in accordance with one example embodiment of the present disclosure.

FIG. 12 is a drawing schematically illustrating experimental results right after the human outer root sheath cells are irradiated with the ultrasound (the pressure: 1 MPa and the duty percentage: 1%) in accordance with one example embodiment of the present disclosure.

Figure 13:
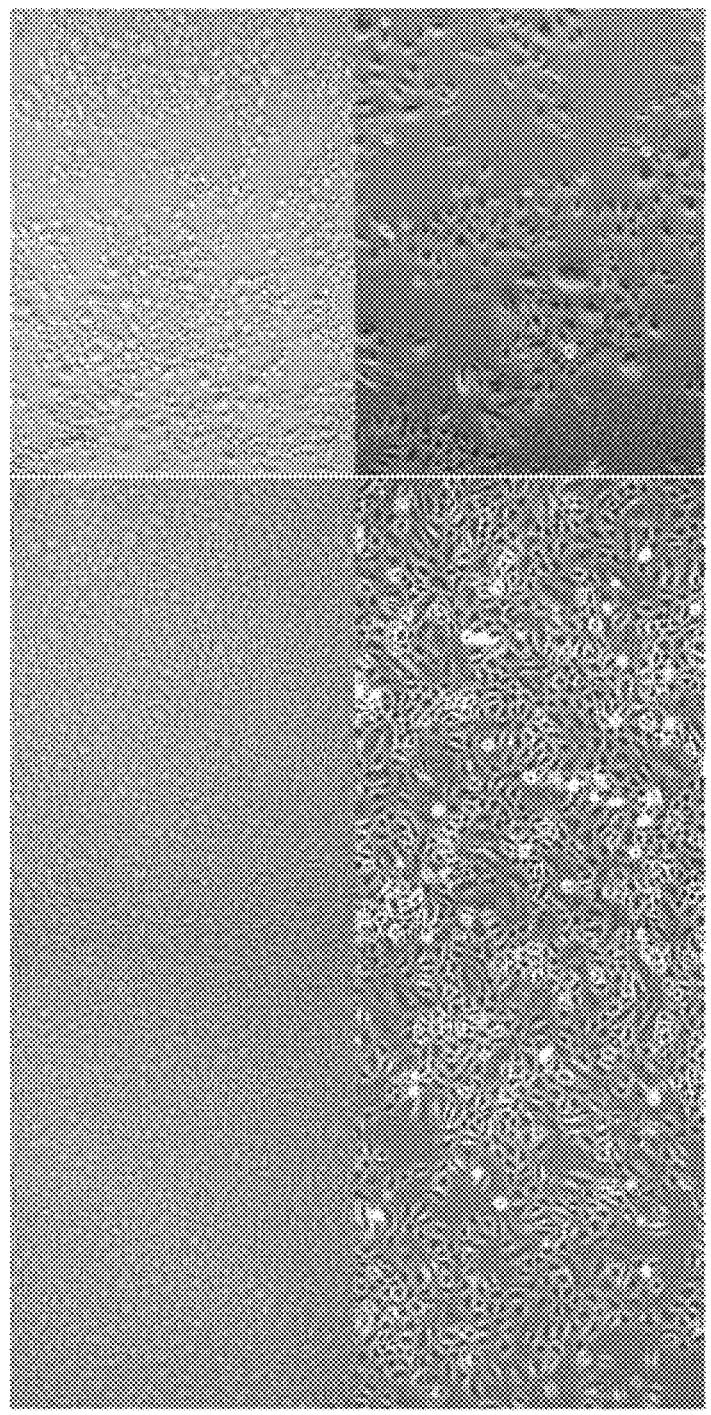
FIG. 13 is a drawing schematically illustrating experimental results 12 hours after the human outer root sheath cells are irradiated with the ultrasound having the pressure of 1 MPa and the duty percentage of 1% in accordance with one example embodiment of the present disclosure.

FIG. 13 is a drawing schematically illustrating experimental results 12 hours after the human outer root sheath cells are irradiated with the ultrasound (the pressure: 1 MPa and the duty percentage: 1%) in accordance with one example embodiment of the present disclosure.

By referring to FIGS. 12 and 13, compared to the results of the control group after 12 hours, a significant increase is observed in the viability of the cells 12 hours after the cells are irradiated with the ultrasound (the pressure: 1 MPa and the duty percentage: 1%).

Figure 14:
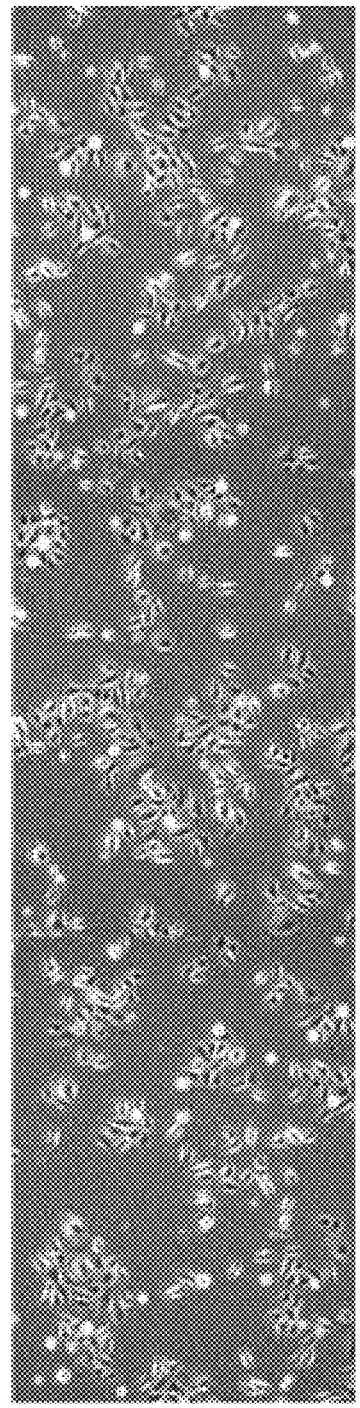
FIG. 14 is a drawing schematically illustrating experimental results right after the human outer root sheath cells are irradiated with the ultrasound having the pressure of 1 MPa and the duty percentage of 2% in accordance with one example embodiment of the present disclosure.

FIG. 14 is a drawing schematically illustrating experimental results right after the human outer root sheath cells are irradiated with the ultrasound (the pressure: 1 MPa and the duty percentage: 2%) in accordance with one example embodiment of the present disclosure.

Figure 15:
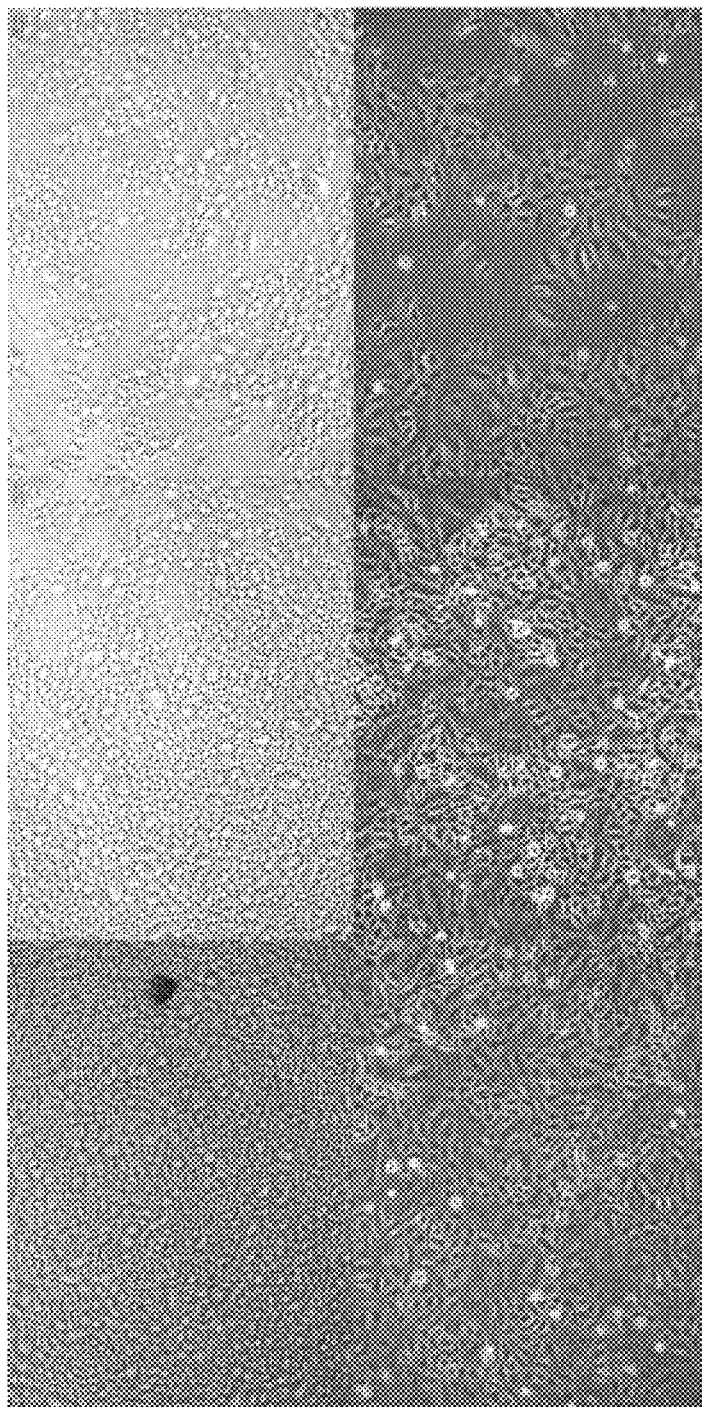
FIG. 15 is a drawing schematically illustrating experimental results 12 hours after the human outer root sheath cells are irradiated with the ultrasound having the pressure of 1 MPa and the duty percentage of 2% in accordance with one example embodiment of the present disclosure.

FIG. 15 is a drawing schematically illustrating experimental results 12 hours after the human outer root sheath cells are irradiated with the ultrasound (the pressure: 1 MPa and the duty percentage: 2%) in accordance with one example embodiment of the present disclosure.

By referring to FIGS. 14 and 15, compared to the results of the control group, a decrease is observed in the viability of the cells, for example, cell bursting or deformation, 12 hours after the cells are irradiated with the ultrasound (the pressure: 1 MPa and the duty percentage: 2%).

Figure 16:
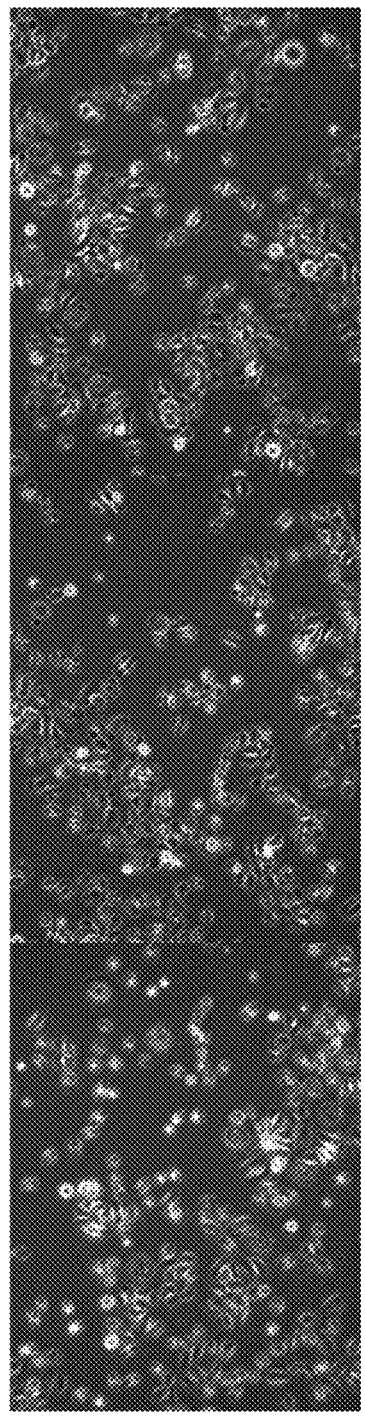
FIG. 16 is a drawing schematically illustrating experimental results right after the human outer root sheath cells are irradiated with the ultrasound having the pressure of 1 MPa and the duty percentage of 3% in accordance with one example embodiment of the present disclosure.

FIG. 16 is a drawing schematically illustrating experimental results right after the human outer root sheath cells are irradiated with the ultrasound (the pressure: 1 MPa and the duty percentage: 3%) in accordance with one example embodiment of the present disclosure.

Figure 17:
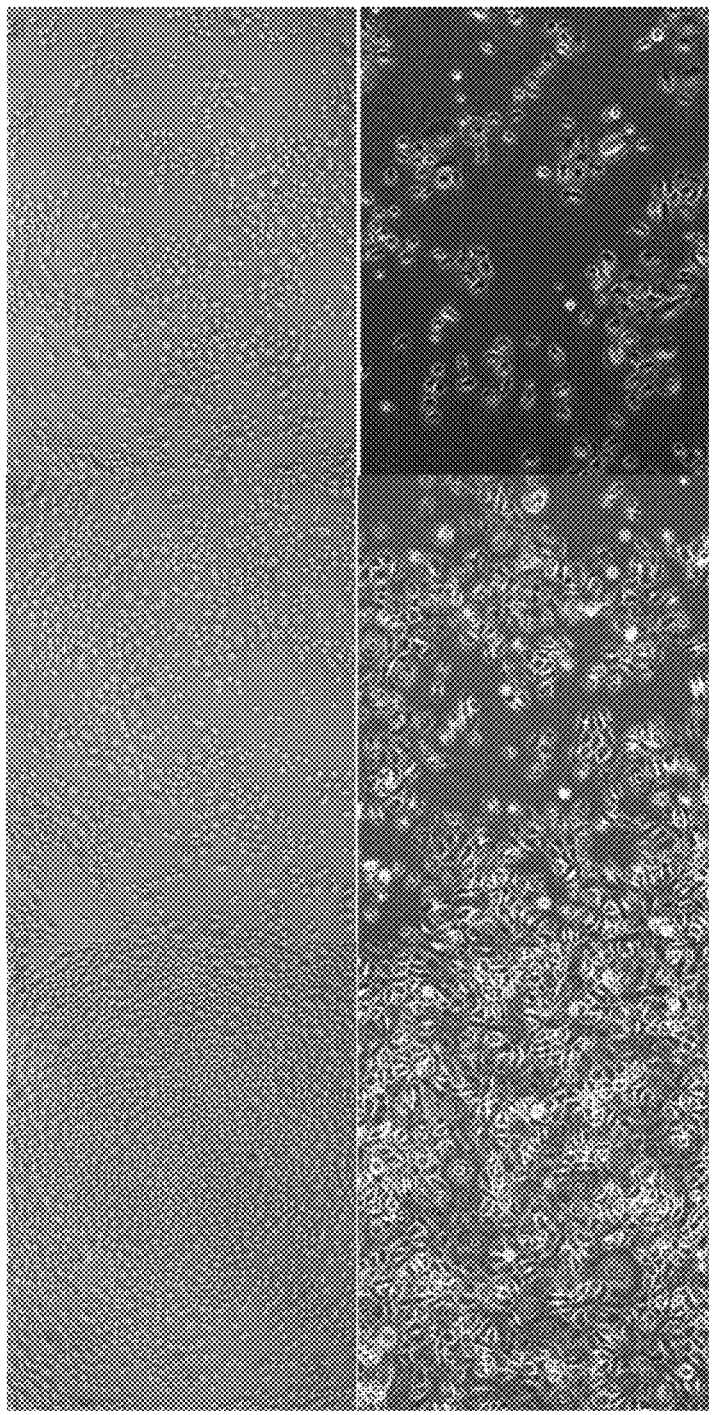
FIG. 17 is a drawing schematically illustrating experimental results 12 hours after the human outer root sheath cells are irradiated with the ultrasound having the pressure of 1 MPa and the duty percentage of 3% in accordance with one example embodiment of the present disclosure.

FIG. 17 is a drawing schematically illustrating experimental results 12 hours after the human outer root sheath cells are irradiated with the ultrasound (the pressure: 1 MPa and the duty percentage: 3%) in accordance with one example embodiment of the present disclosure.

By referring to FIGS. 16 and 17, compared to the results of the control group, a decrease is observed in the viability of the cells, for example, the cell bursting or the deformation, at the time of the ultrasound irradiation and 12 hours after the ultrasound irradiation (the pressure: 1 MPa and the duty percentage: 3%).

Figure 18:
FIG. 18 is a drawing schematically illustrating experimental results right after the human outer root sheath cells are irradiated with the ultrasound having the pressure of 1.5 MPa and the duty percentage of 5% in accordance with one example embodiment of the present disclosure.

FIG. 18 is a drawing schematically illustrating experimental results right after the human outer root sheath cells are irradiated with the ultrasound (the pressure: 1.5 MPa and the duty percentage: 5%) in accordance with one example embodiment of the present disclosure.

Figure 19:
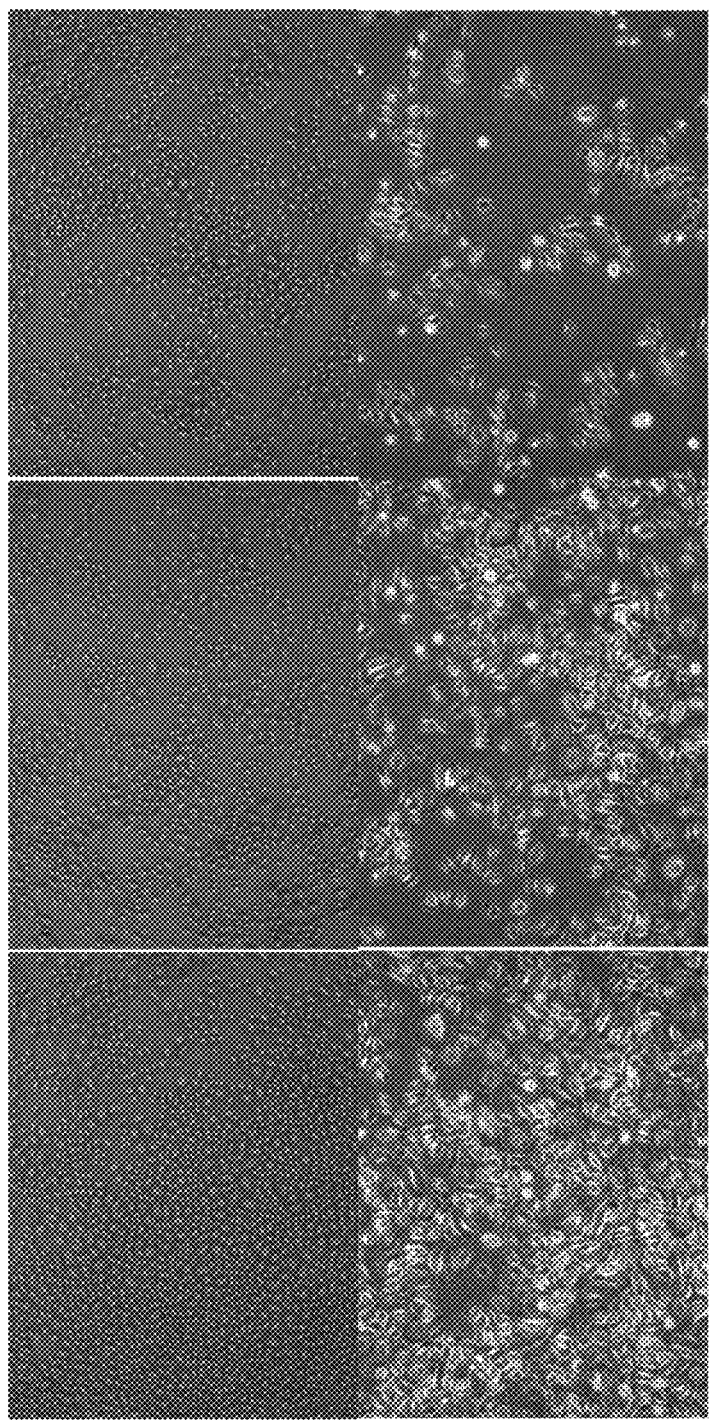
FIG. 19 is a drawing schematically illustrating experimental results 12 hours after the human outer root sheath cells are irradiated with the ultrasound having the pressure of 1.5 MPa and the duty percentage of 5% in accordance with one example embodiment of the present disclosure.

FIG. 19 is a drawing schematically illustrating experimental results 12 hours after the human outer root sheath cells are irradiated with the ultrasound (the pressure: 1.5 MPa and the duty percentage: 5%) in accordance with one example embodiment of the present disclosure.

By referring to FIGS. 18 and 19, compared to the results of the control group, a decrease is observed in the viability of the cells, for example, the cell bursting or the deformation with a high ratio, at the time of the ultrasound irradiation and 12 hours after the ultrasound irradiation (the pressure: 1.5 MPa and the duty percentage: 5%).

Figure 20:
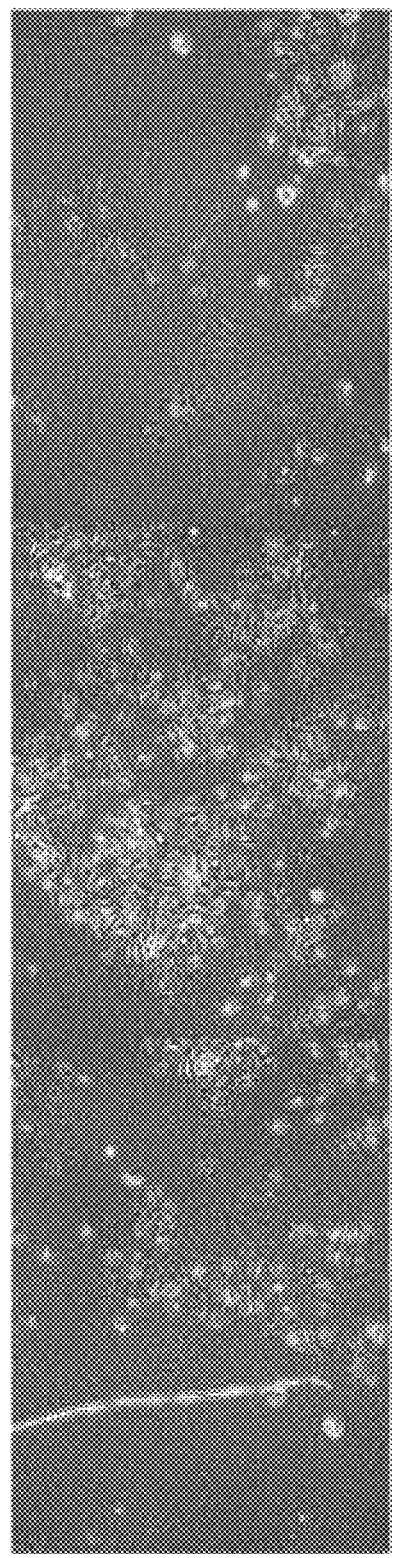
FIG. 20 is a drawing schematically illustrating experimental results right after the human outer root sheath cells are irradiated with the ultrasound having the pressure of 1.5 MPa and the duty percentage of 10% in accordance with one example embodiment of the present disclosure.

FIG. 20 is a drawing schematically illustrating experimental results right after the human outer root sheath cells are irradiated with the ultrasound (the pressure: 1.5 MPa and the duty percentage: 10%) in accordance with one example embodiment of the present disclosure.

Figure 21:
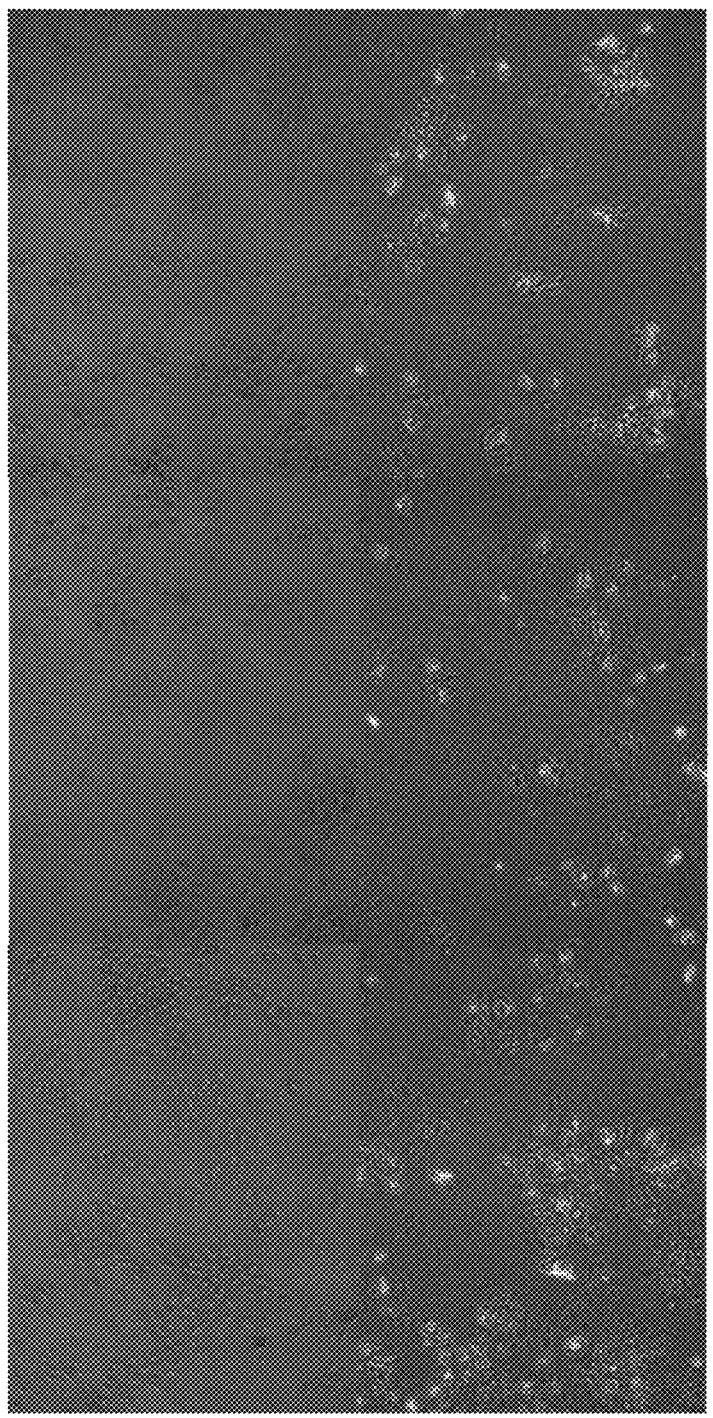
FIG. 21 is a drawing schematically illustrating experimental results 12 hours after the human outer root sheath cells are irradiated with the ultrasound having the pressure of 1.5 MPa and the duty percentage of 10% in accordance with one example embodiment of the present disclosure.

FIG. 21 is a drawing schematically illustrating experimental results 12 hours after the human outer root sheath cells are irradiated with the ultrasound (the pressure: 1.5

MPa and the duty percentage: 10%) in accordance with one example embodiment of the present disclosure.

By referring to FIGS. 20 and 21, compared to the results of the control group, a decrease is observed in the viability of the cells, for example, the cell bursting or the deformation of most of the cells, at the time of the ultrasound irradiation and 12 hours after the ultrasound irradiation (the pressure: 1.5 MPa and the duty percentage: 10%).

As such, by referring to FIGS. 5 to 21, the ultrasound of the pressure of 1 MPa or less, the duty percentage of 5% or less, and the intensity of 416.7 mW/cm$^2$ or less is confirmed to be safe for the cells. In addition, when the pressure was set to 1.5 MPa or more, the cell bursting or the deformation is observed. Also, compared to the control group, an increase in growth of the cells is observed when the cells are irradiated with the ultrasound in a safe energy range.

As an example, in accordance with the method for increasing the viability of the cells by irradiating the cells with the ultrasound, on condition that the ultrasound parameters have been preset within respective ranges, the ultrasound irradiating device may position an ultrasonic transducer within a threshold range from epidermis of a subject and then may irradiate the epidermis with the ultrasound. Herein, the ultrasound parameters may include the pressure of the ultrasound and the duty percentage of the ultrasound. Further, the pressure of the ultrasound may range from 0.5 MPa to 1 MPa and the duty percentage of the ultrasound may range from 1% to 5%.

Also, the ultrasound parameters may further include the intensity of the ultrasound, which may be in a range from 166.7 mW/cm$^2$ to 416.7 mW/cm$^2$.

Also, the ultrasound parameters may further include a total time of the ultrasound irradiation which may be ten minutes, but the scope of the present disclosure is not limited thereto and the total time of the ultrasound irradiation may be shorter or longer than ten minutes.

In addition, the ultrasonic transducer may irradiate the epidermis of the subject with the ultrasound, in contact with the epidermis or at a certain distance from the epidermis. In addition, the ultrasonic transducer may have a shape surrounding the epidermis of the subject in a form of a helmet or a headgear.

Also, the cells may be the outer root sheath cells.

Figure 22:
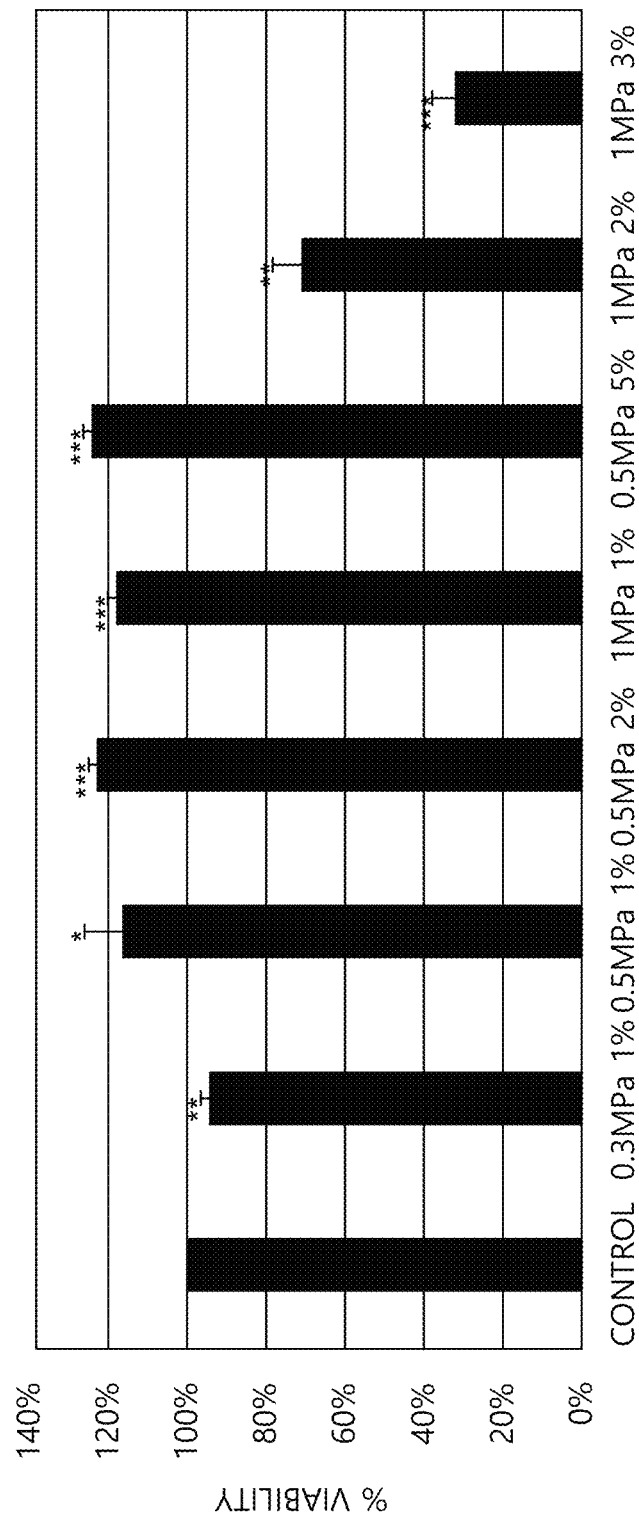
FIG. 22 is a drawing schematically illustrating experimental results of the viability of the human outer root sheath cells with respect to the pressure and the duty percentage of the ultrasound as independent variables in accordance with one example embodiment of the present disclosure.

FIG. 22 is a drawing schematically illustrating the experimental results of the viability of the human outer root sheath cells derived from irradiating the cells with the ultrasound having the various pressures and the duty percentages in accordance with one example embodiment of the present disclosure. And FIGS. 23 and 24 are drawings schematically illustrating the experimental results of the viability of the human outer root sheath cells derived from irradiating the cells with the ultrasound having the various intensities in accordance with one example embodiment of the present disclosure.

Figure 23:
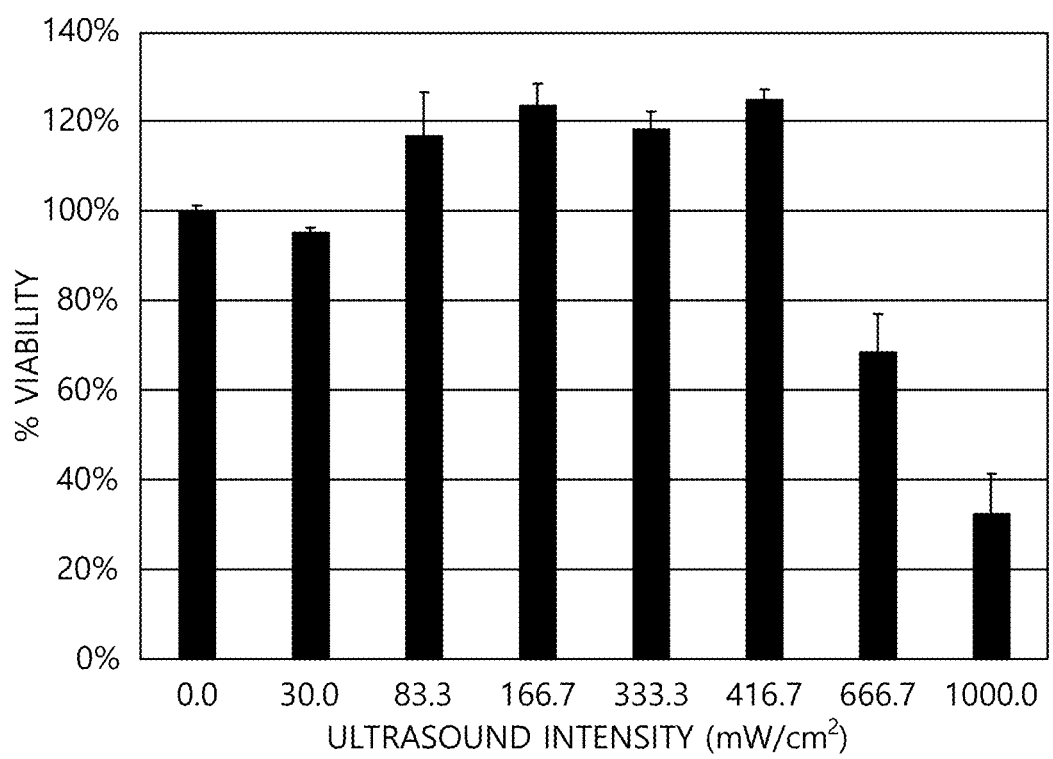
FIGS. 23 and 24 are drawings schematically illustrating experimental results of the viability of the human outer root sheath cells with respect to an intensity of the ultrasound as an independent variable in accordance with one example embodiment of the present disclosure.
Figure 24:
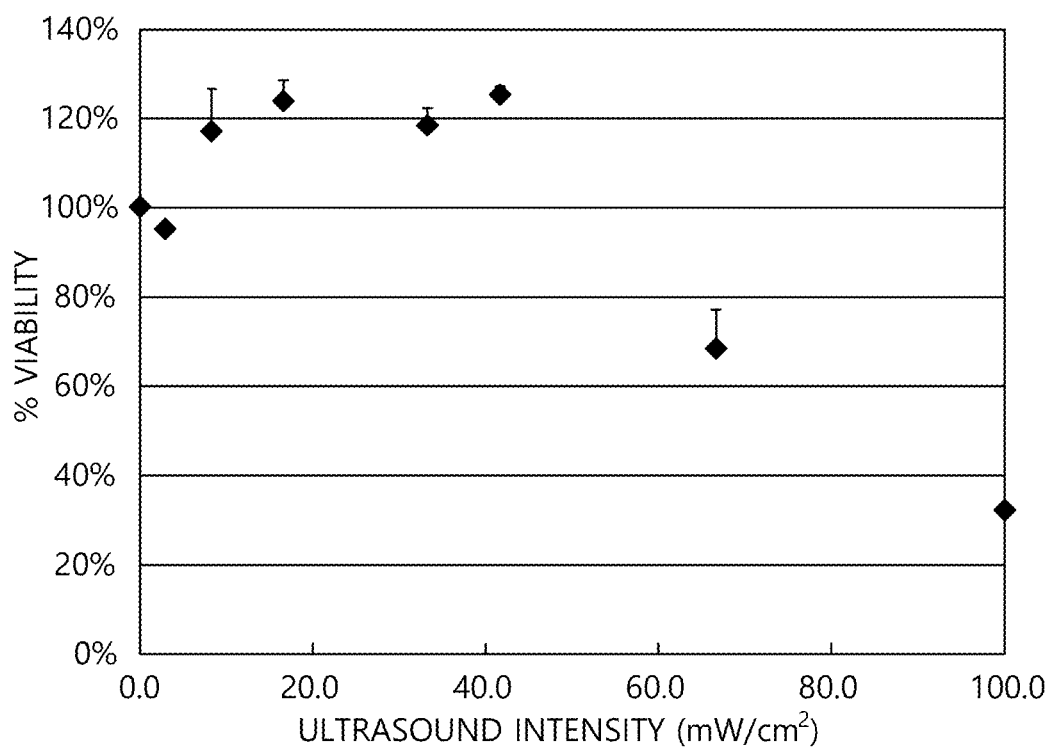

As can be seen from FIGS. 22 to 24, significantly higher viabilities of the cells are observed when irradiated with the ultrasound having the ultrasound parameters representing (i) the pressure ranging from 0.5 MPa to 1 MPa, (ii) the duty percentage ranging from 1% to 5%, and (iii) the intensity ranging from 166.7 mW/cm$^2$ to 416.7 mW/cm$^2$, compared to the ultrasound with the ultrasound parameters outside such ranges.

For reference, a Table 11 below describes the measured viabilities of the cells according to the pressure and the duty percentage of the ultrasound with which the cells are irradiated.

TABLE 11

|  | av | sd |
|---|---|---|
| Control | 100% | 0.01 |
| 0.3 MPa 1% | 95% | 0.01 |
| 0.5 MPa 1% | 117% | 0.09 |
| 0.5 MPa 2% | 124% | 0.05 |
| 0.5 MPa 5% | 125% | 0.02 |
| 1 MPa 1% | 118% | 0.04 |
| 1 MPa 2% | 68% | 0.08 |
| 1 MPa 3% | 32% | 0.09 |

Meanwhile, the ultrasound parameters may further include the frequency of the ultrasound which may range from 0.5 MHz to 4.6 MHz.

Figure 25:
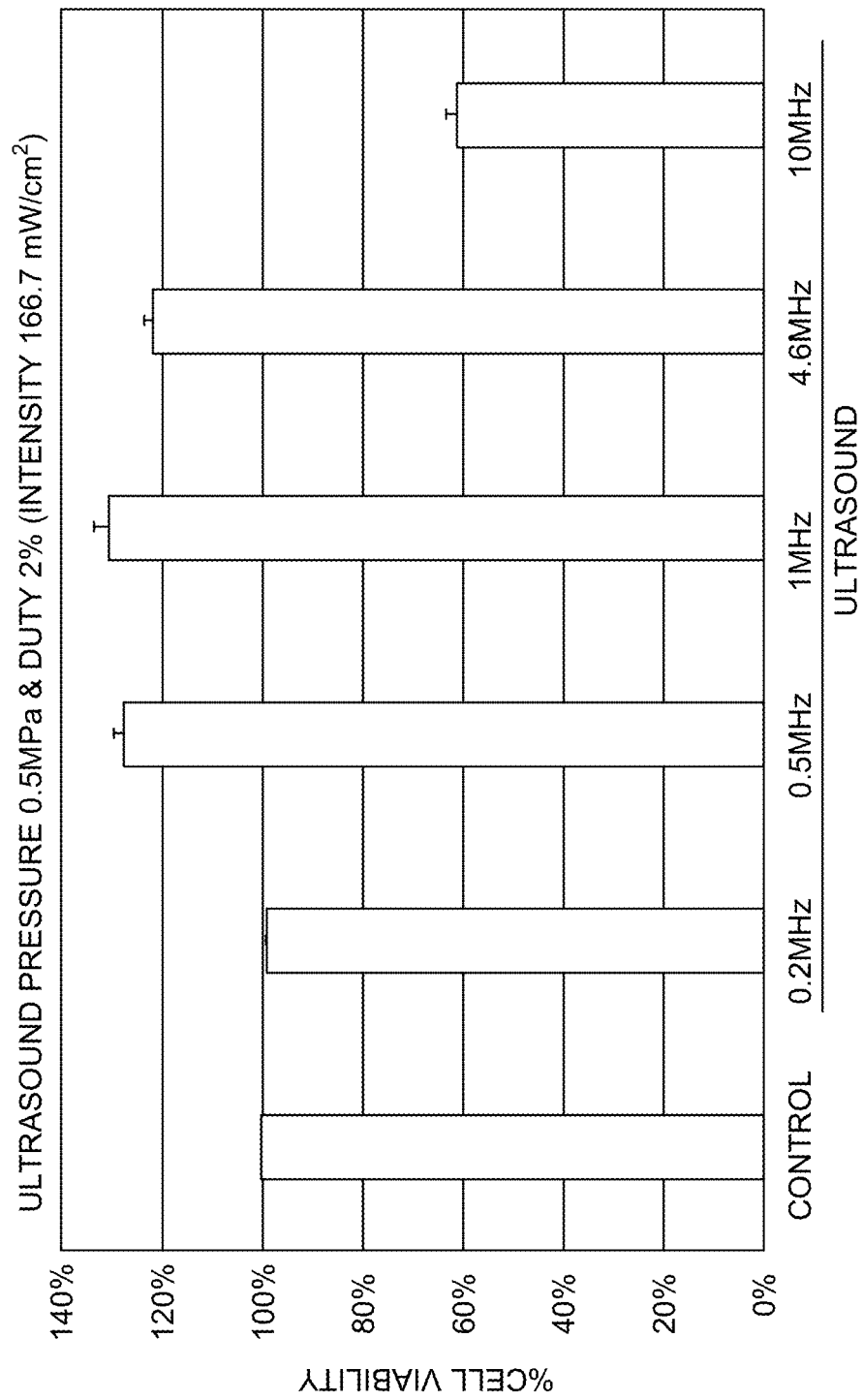
FIG. 25 is a drawing schematically illustrating experimental results of irradiating the human outer root sheath cells with the ultrasound having the pressure of 0.5 MPa, the duty percentage of 2%, the intensity of 166.7 mW/cm$^2$, with respect to a frequency of the ultrasound in accordance with one example embodiment of the present disclosure.
Figure 26:
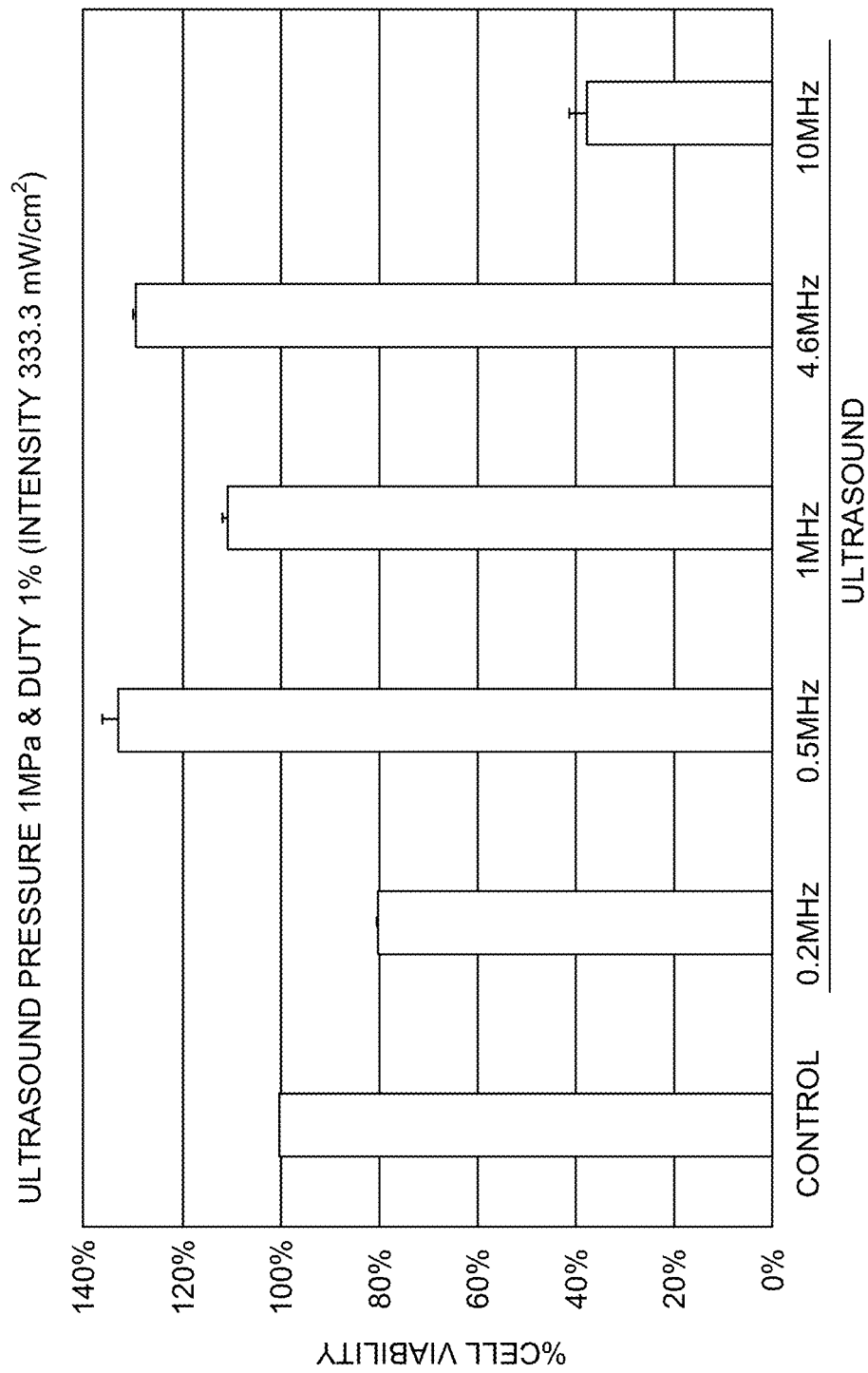
FIG. 26 is a drawing schematically illustrating experimental results of irradiating the human outer root sheath cells with the ultrasound having the pressure of 1 MPa, the duty percentage of 1%, the intensity of 333.3 mW/cm², with respect to the frequency of the ultrasound in accordance with one example embodiment of the present disclosure.
Figure 27:
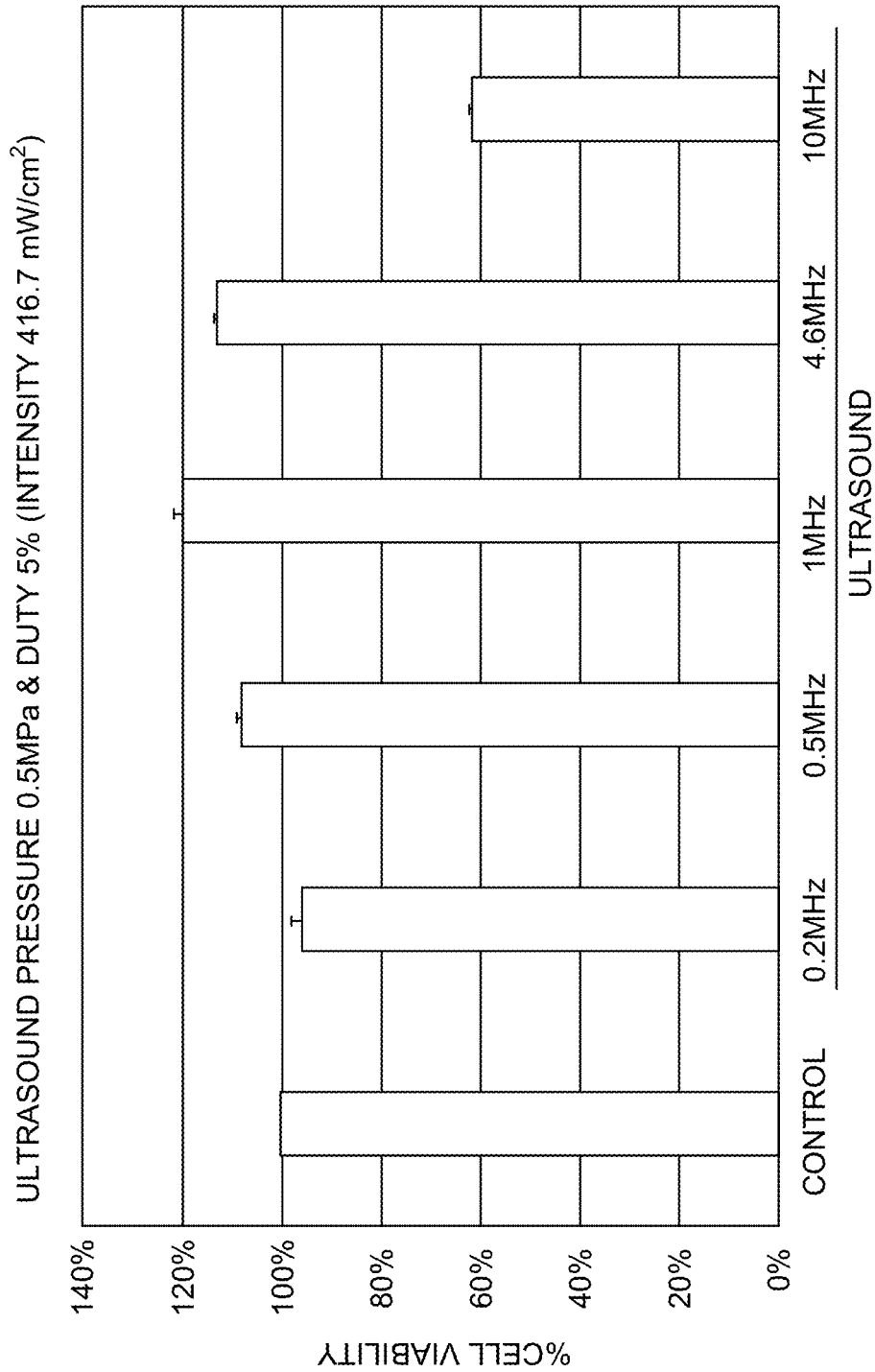
FIG. 27 is a drawing schematically illustrating experimental results of irradiating the human outer root sheath cells with the ultrasound having the pressure of 0.5 MPa, the duty percentage of 5%, the intensity of 416.7 mW/cm², with respect to the frequency of the ultrasound in accordance with one example embodiment of the present disclosure.

FIGS. 25 to 27 are drawings schematically illustrating experimental results of irradiating the human outer root sheath cells with the ultrasound of varying frequencies, while the pressure and the duty percentage are fixed, in accordance with one example embodiment of the present disclosure.

As an example, FIG. 25 is a drawing schematically illustrating experimental results of irradiating the human outer root sheath cells with the ultrasound (the pressure: 0.5 MPa, the duty percentage: 2%, and the intensity: 166.7 mW/cm$^2$) and the varying frequencies of 0.2 MHz, 0.5 MHz, 1 MHz, 4.6 MHz, and 10 MHz in accordance with one example embodiment of the present disclosure.

As can be seen in FIG. 25, significantly higher viabilities of the cells are observed in a range from 0.5 MHz to 4.6 MHz of the ultrasound, compared to the viabilities of the cells outside the range.

As another example, FIG. 26 shows experimental results of irradiating the human outer root sheath cells with the ultrasound (the pressure: 1 MPa, the duty percentage: 1%, and the intensity: 333.3 mW/cm$^2$) and the varying frequencies of 0.2 MHz, 0.5 MHz, 1 MHz, 4.6 MHz, and 10 MHz in accordance with one example embodiment of the present disclosure.

As can be seen in FIG. 26, significantly higher viabilities of the cells are observed in a range from 0.5 MHz to 4.6 MHz of the ultrasound, compared to the viabilities of the cells outside the range.

As another example, FIG. 27 shows experimental results of irradiating the human outer root sheath cells with the ultrasound (the pressure: 0.5 MPa, the duty percentage: 5%, and the intensity: 416.7 mW/cm$^2$), and the varying frequencies of 0.2 MHz, 0.5 MHz, 1 MHz, 4.6 MHz, and 10 MHz in accordance with one example embodiment of the present disclosure.

As can be seen in FIG. 27, significantly higher viabilities of the cells are observed in a range from 0.5 MHz to 4.6 MHz of the ultrasound, compared to the viabilities of the cells outside the range.

FIGS. 28 to 31 are drawings schematically illustrating experimental results of the gene expression when the human outer root sheath cells are irradiated with the ultrasound having the frequency of 1 MHz while varying the pressure and the duty percentage in accordance with one example embodiment of the present disclosure.

Figure 28:
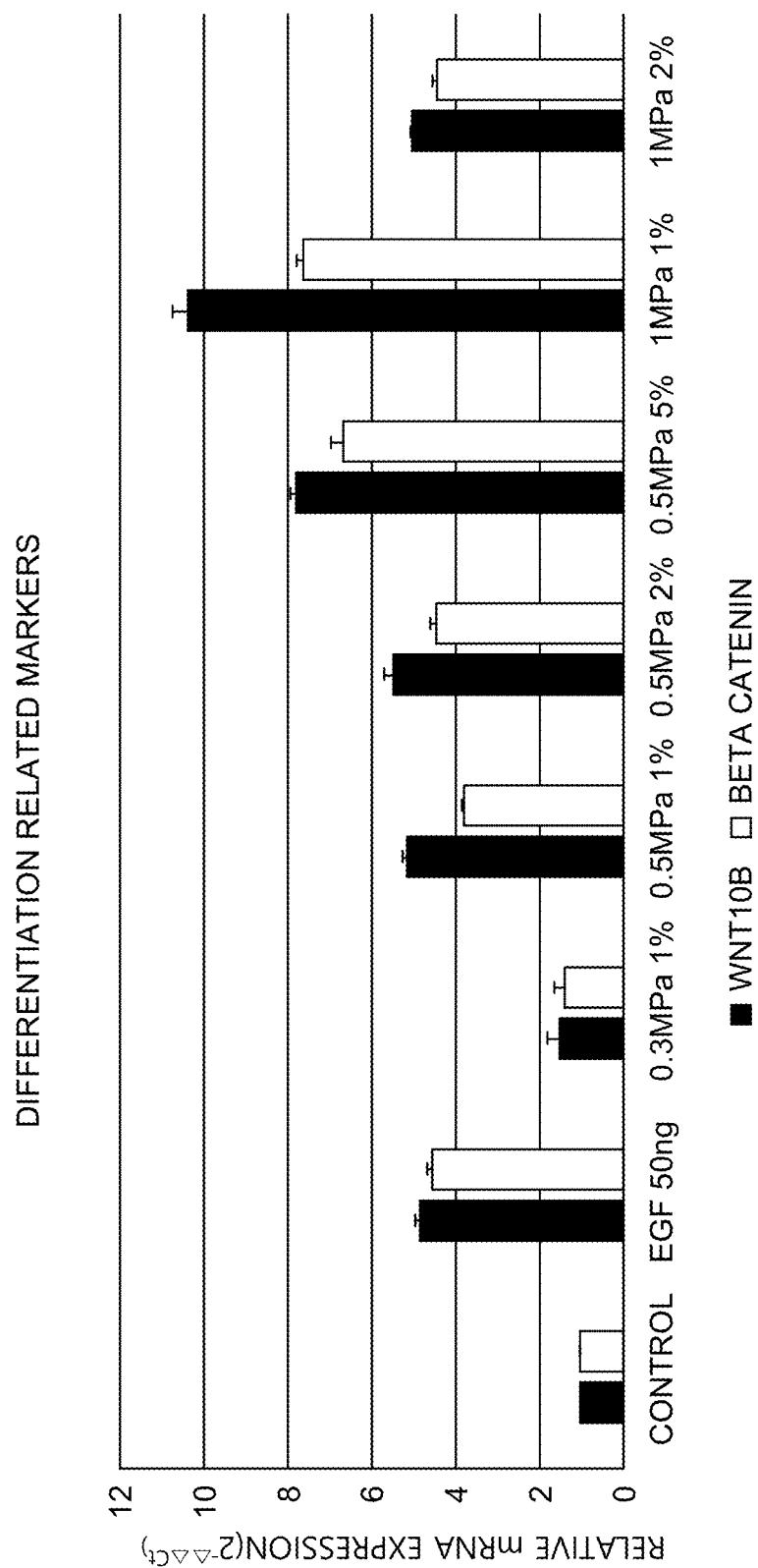

Specifically, FIG. 28 shows experimental results of gene expression of WNT10B and Beta Catenin related genes when the human outer root sheath cells are irradiated with the ultrasound having the frequency of 1 MHz while varying the pressure and the duty percentage in accordance with one example embodiment of the present disclosure. When the human outer root sheath cells are irradiated with the ultrasound having the intensity set to 166.7 mW/cm² (0.5 MPa, 2%), 333.3 mW/cm² (1 MPa, 1%) and 416.7 mW/cm² (0.5 MPa, 5%), WNT10B and Beta Catenin related gene expression levels are observed as significantly higher than those of the control group.

Figure 29:
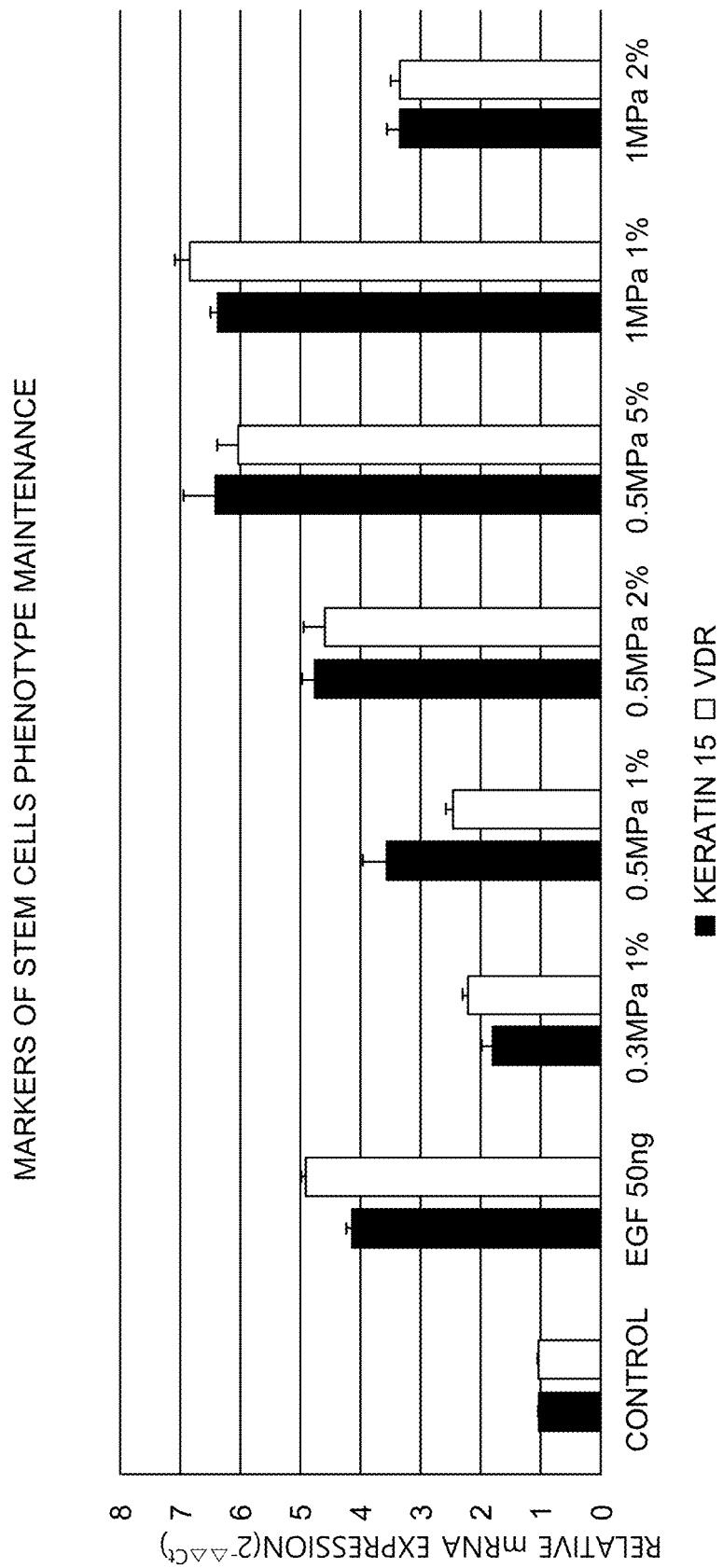

Also, FIG. 29 shows experimental results of gene expression of Keratin 15 and VDR related genes when the human outer root sheath cells are irradiated with the ultrasound having the frequency of 1 MHz while varying the pressure and the duty percentage in accordance with one example embodiment of the present disclosure. As shown in FIG. 28, when the human outer root sheath cells are irradiated with the ultrasound having the intensity set to 166.7 mW/cm² (0.5 MPa, 2%), 333.3 mW/cm² (1 MPa, 1%) and 416.7 mW/cm² (0.5 MPa, 5%), the Keratin 15 and VDR related gene expression levels are observed as significantly higher than those of the control group.

Also, FIG. 30 shows experimental results of gene expression of PCNA and Ki67 related genes when the human outer root sheath cells are irradiated with the ultrasound having the frequency of 1 MHz while varying the pressure and the duty percentage in accordance with one example embodiment of the present disclosure. As shown in FIG. 28, when the human outer root sheath cells are irradiated with the ultrasound having the intensity set to 166.7 mW/cm² (0.5 MPa, 2%), 333.3 mW/cm² (1 MPa, 1%) and 416.7 mW/cm² (0.5 MPa, 5%), the PCNA and Ki67 related gene expression levels are observed as significantly higher than those of the control group.

Also, FIG. 31 shows experimental results of gene expression of BCL2 related genes when the human outer root sheath cells are irradiated with the ultrasound having the frequency of 1 MHz while varying the pressure and the duty percentage in accordance with one example embodiment of the present disclosure. As shown in FIG. 28, when the human outer root sheath cells are irradiated with the ultrasound having the intensity set to 166.7 mW/cm² (0.5 MPa, 2%), 333.3 mW/cm² (1 MPa, 1%) and 416.7 mW/cm² (0.5 MPa, 5%), the BCL2 related gene expression levels are observed as significantly higher than those of the control group.

Meanwhile, the ultrasound parameters may further include PRF or PRP. Herein, PRF may range from 1 Hz to 100 Hz and PRP may range from 0.01 second to 1 second.

The present disclosure has an effect of increasing the viability of the cells in a non-invasive and painless manner by irradiating the cells with the ultrasound.

The present disclosure has another effect of increasing the viability of the cells only by irradiating the cells with the ultrasound without using expensive drugs.

As seen above, the present disclosure has been explained by specific matters such as detailed components, limited embodiments, and drawings. They have been provided only to help more general understanding of the present disclosure. It, however, will be understood by those skilled in the art that various changes and modification may be made from the description without departing from the spirit and scope of the disclosure as defined in the following claims.

Accordingly, the spirit of the present disclosure must not be confined to the explained embodiments, and the following patent claims as well as everything including variations equal or equivalent to the patent claims pertain to the category of the spirit of the present disclosure.

What is claimed is:

1. A method for irradiating one or more cells with ultrasound, comprising a step of:
   on condition that ultrasound parameters have been preset within respective ranges, an ultrasound irradiating device positioning an ultrasonic transducer within a threshold range from epidermis of a subject and then irradiating the epidermis with the ultrasound,
   wherein the ultrasound parameters include pressure of the ultrasound and duty percentage of the ultrasound, wherein the pressure of the ultrasound ranges from 0.5 MPa to 1 MPa, and wherein the duty percentage of the ultrasound ranges from 1% to 5%,
   wherein, the ultrasound parameters further include intensity of the ultrasound, frequency of the ultrasound, total irradiation time of the ultrasound, and PRF (pulse repetition frequency) of the ultrasound,
   wherein, the intensity of the ultrasound ranges from 166.7 mW/cm² to 416.7 mW/cm²,
   wherein, the frequency of the ultrasound ranges from 0.5 MHz to 4.6 MHz,
   wherein, the total irradiation time is equal to or less than ten minutes,
   wherein, the PRF of the ultrasound ranges from 1 Hz to 100 Hz,
   wherein, the cells are outer root sheath cells.

2. An ultrasound irradiating device for irradiating one or more cells with ultrasound, comprising:
   an ultrasonic transducer; and
   a controlling part, on condition that ultrasound parameters have been preset within respective ranges, for positioning the ultrasonic transducer within a threshold range from epidermis of a subject and then allowing the ultrasonic transducer to irradiate the epidermis with the ultrasound; and
   wherein the ultrasound parameters include a pressure of the ultrasound and a duty percentage of the ultrasound, wherein the pressure of the ultrasound ranges from 0.5 MPa to 1 MPa, and wherein the duty percentage of the ultrasound ranges from 1% to 5%,
   wherein, the ultrasound parameters further include intensity of the ultrasound, frequency of the ultrasound, total irradiation time of the ultrasound, and PRF (pulse repetition frequency) of the ultrasound,
   wherein, the intensity of the ultrasound ranges from 166.7 mW/cm² to 416.7 mW/cm²,
   wherein, the frequency of the ultrasound ranges from 0.5 MHz to 4.6 MHz,
   wherein, the total irradiation time is equal to or less than ten minutes,
   wherein, the PRF of the ultrasound ranges from 1 Hz to 100 Hz,
   wherein, the cells are outer root sheath cells.

* * * * *